US009662329B2

(12) United States Patent
Chang et al.

(10) Patent No.: US 9,662,329 B2
(45) Date of Patent: May 30, 2017

(54) USE OF SURVIVIN ANTAGONISTS IN POLYOMAVIRUS-RELATED DISEASE

(71) Applicant: University of Pittsburgh—Of the Commonwealth System of Higher Education, Pittsburgh, PA (US)

(72) Inventors: Yuan Chang, Pittsburgh, PA (US); Patrick S. Moore, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 105 days.

(21) Appl. No.: 14/388,418

(22) PCT Filed: Mar. 26, 2013

(86) PCT No.: PCT/US2013/033836
§ 371 (c)(1),
(2) Date: Sep. 26, 2014

(87) PCT Pub. No.: WO2013/148649
PCT Pub. Date: Oct. 3, 2013

(65) Prior Publication Data
US 2015/0086535 A1 Mar. 26, 2015

Related U.S. Application Data

(60) Provisional application No. 61/615,546, filed on Mar. 26, 2012.

(51) Int. Cl.
*A61K 31/497* (2006.01)
*A61K 45/06* (2006.01)
*C12N 15/113* (2010.01)
*A61K 31/713* (2006.01)

(52) U.S. Cl.
CPC .......... *A61K 31/497* (2013.01); *A61K 31/713* (2013.01); *A61K 45/06* (2013.01)

(58) Field of Classification Search
None
See application file for complete search history.

(56) References Cited

U.S. PATENT DOCUMENTS

| 8,003,105 | B2 | 8/2011 | Nakahara et al. |
| 2003/0114508 | A1 | 6/2003 | Matsuhisa et al. |
| 2006/0223831 | A1 | 10/2006 | Kinoyama et al. |
| 2011/0098651 | A1 | 4/2011 | Falo, Jr. et al. |

FOREIGN PATENT DOCUMENTS

| EP | 1256576 A1 | 11/2002 |
| EP | 1614686 A1 | 1/2006 |
| WO | 2009048560 A1 | 4/2009 |
| WO | 2012027379 A2 | 3/2012 |

OTHER PUBLICATIONS

Abstract of Houben et al, Experimental Dermatology, 2010, vol. 19, No. 2, p. 209, abstract No. P254.*
Abstract of Raest et al, Journal of Pediatric Hematology and Oncology, 2014, vol. 36, pp. 458-463.*
Robinson, PLoS Biology, 2004, vol. 2, No. 1, pp. 00180-00020.*
Holmes, Nature Medicine, Jun. 2012, vol. 18, pp. 842-843.*
Ashburner et al., "Gene Ontology: tool for the unification of biology", Nature Genetics, May 2000, pp. 25-29, 25.
Czarna et al., "Robust Generation of Lead Compounds for Protein-Protein Interactions by Computational and MCR Chemistry: p53/Hdm2 Antagonists", Angew Chem iNT eD eNGL, Jul. 19, 2010, pp. 5352-5356, 49(31).
Einsele, "Bortezomib", Recent Results Cancer Res, 2010, pp. 173-187, 184.
Feng et al., "Cellular and Viral Factors Regulating Merkel Cell Polyomavirus Replication", PloS one, 2001, pp. 1-12, e22468.
Feng et al., "Clonal Integration of a Polyomavirus in Human Merkel Cell Carcinoma", Science, Feb. 22, 2008, pp. 1096-1100, 319(5866).
Houben et al., "Merkel Cell Polyomavirus-Infected Merkel Cell Carcinoma Cells Require Expression of Viral T Antigens", J. Virol, 2010, pp. 7064-7072, vol. 84, No. 14.
Iwasa et al., "Marked anti-tumour activity of the combination of YM155, a novel survivin suppressant, and platinum-based drugs", Br J Cancer, Jun. 29, 2010, pp. 36-42, 103.
Kim et al., "Nuclear expression of survivin portends a poor prognosis in Merkel cell carcinoma", Modern Pathology, 2008, pp. 764-769, vol. 21, No. 6.
Leblanc et al., "Proteasome Inhibitor PS-341 Inhibits Human Myeloma Cell Growth in Vivo and Prolongs Survival in a Murine Model", Cancer Res, Sep. 1, 2002, pp. 4996-5000 62, 4996.
Lewis et al., "A multi-center phase II evaluation of the small molecule survivin suppressor YM155 in patients with unresectable stage III or IV melanoma", Invest. New Drugs, 2011, pp. 161-166, vol. 29.
Nakahara et al., "Broad spectrum and potent antitumor activities of YM155, a novel small-molecule survivin suppressant, in a wide variety of human cancer cell lines and xenograft models", Cancer Science, 2011, pp. 614-621, vol. 102, No. 3.
Nakahara et al., "YM155, A Novel Small-Molecule Survivin Suppressant, Induces Regression of Established Human Hormone-Refractor Prostate Tumor Xenografts", Cancer Res, Sep. 1, 2007, pp. 8014-8021, vol. 67, No. 17.

(Continued)

*Primary Examiner* — Karen Canella
(74) *Attorney, Agent, or Firm* — The Webb Law Firm

(57) ABSTRACT

A method of treating a polyomavirus (+) cancer in which survivin is upregulated in a patient is provided, comprising administering to the patient a therapeutically effective amount of a composition that downregulates survivin expression or function in cells of the polyomavirus (+) cancer. A method of reducing growth of polyomavirus (+) cancer cells in which survivin is up-regulated is provided, comprising contacting the cells with an amount of a composition that downregulates survivin expression or function effective to reduce growth of the cells. Also provided is sepantronium salt, for use in treating a polyomavirus (+) cancer in which survivin is up-regulated.

15 Claims, 31 Drawing Sheets

(56) References Cited

OTHER PUBLICATIONS

Nakahara et al., "YM155, a novel survivin suppressant, enhances taxane-induced apoptosis and tumor regression in a human calu 6 lung cancer xenograft model", Anticancer Drugs, Jun. 2011, pp. 454-462, 22.

Nakahara et al., "Interleukin Enhancer-Binding Factor 3/NF110 is a Target of YM155, A Suppressant of Survivin", Mol Cell Proteomics, 2012, pp. M111.013243.1-6, vol. 11, No. 7.

Ohtani et al., "Regulation of the cyclin E gene by transcription factor E2F1", Proceedings of the National Academy of Sciences of the United States of America, Dec. 1995, pp. 12146-12150, 92.

Petre et al., "Functional p53 Signaling in Kaposi's Sarcoma-Associated Herpesvirus Lymphomas: Implications for Therapy", J Virol 81, Feb. 2007, pp. 1912-1922, vol. 81.

Pfaffl, "A new mathematical model for relative quantification in real-time RT-PCR", Nucleic Acids Research, 2001, pp. 2002-2007, vol. 29, No. 20.

Pina-Oviedo et al., "Effects of JC Virus Infection on Anti-Apoptotic Protein Survivin in Progressive Multifocal Leukoencephalopathy", Am. J. Pathology, Apr. 2007, pp. 1291-1303, vol. 170, No. 4.

Popowicz et al., "Structures of low molecular weight inhibitors bound to MDMX and MDM2 reveal new approaches for p53-MDMX/MDM2 antagonist drug discovery", Cell Cycle, Mar. 15, 2010, pp. 1104-1111.

Ronan et al., "Merkel cell carcinoma: In vitro and in vivo characteristics of a new cell line", J Am Acad Dermatol, 1993, pp. 715-722, 29.

Rosen et al., "Establishment and Characterization of a Neuroendocrine Skin Carcinoma Cell Line", Lab Invest, Mar. 1987, pp. 302-312, vol. 56, No. 3.

Sarek et al., "Reactivation of the p53 pathway as a treatment modality for KSHV-induced lymphomas", J Clin Invest, Apr. 2007, pp. 1019-1028, vol. 117, No. 4.

Seguin et al., "High-Throughput Screening Identities a Bisphenol Inhibitor of SV40 Large T Antigen ATPase Activity", Journal of Biomolecular Screening, Feb. 2012, pp. 194-203, 17(2).

Shuda et al., "Human Merkel cell polyomavirus small T antigen is an oncoprotein targeting the 4E-BP1 translation regulator", J of Clin Invest, Sep. 2011, pp. 3623-3634.

Shuda et al., "T antigen mutations are a human tumor-specific signature for Merkel cell polyomavirus", Proc Natl Acad Sci USA, Oct. 21, 2008, pp. 16272-16277, vol. 105, No. 42.

Tolcher et al., "Phase I and Pharmacokinetic Study of YM155, A Small-Molecule Inhibitor of Survivin", J. Clin. Oncol., Nov. 10, 2008; pp. 5198-5203, vol. 26, No. 32.

Tolcher et al., "A phase II study of YM155, a novel small-molecule suppressor of survivin, in castration-resistant axane-pretreated prostate cancer", Ann. Oncol., 2012, pp. 968-973, vol. 23, No. 4.

Tu et al., "Suppression of Survivin Expression Inhibits in Vivo Tumorigenicity and Angiogenesis in Gastric Cancer", Cancer Research, Nov. 15, 2003, pp. 7724-7732, 63.

Yamauchi et al., "Sepantronium Bromide (YM155) induces disruption of the ILF3/p54(nrb) complex, which is required for survivin expression", Biochem Biophys Res Comm, 2012, pp. 711-716, vol. 425.

Wright et al., "Inhibition of Simian Virus 40 replication by targeting the molecular chaperone function and ATPase activity of T antigen", Virus Res, Apr. 2009, pp. 71-80, 141(1).

Zhang et al., "Survivin knockdown by short haiipin RNA abrogates the growth of human hepatocellular carcinoma kenografts in nude mice", Cancer Gene Therapy 17, pp. 275-288.

Zhao et al., "Bayesian Hierarchical Changepoint Methods in Modeling the Tumor Growth Profiles in Xenograft Experiments", Clinical Cancer Res, Mar. 1, 2011, pp. 1057-1064, 17(5).

\* cited by examiner

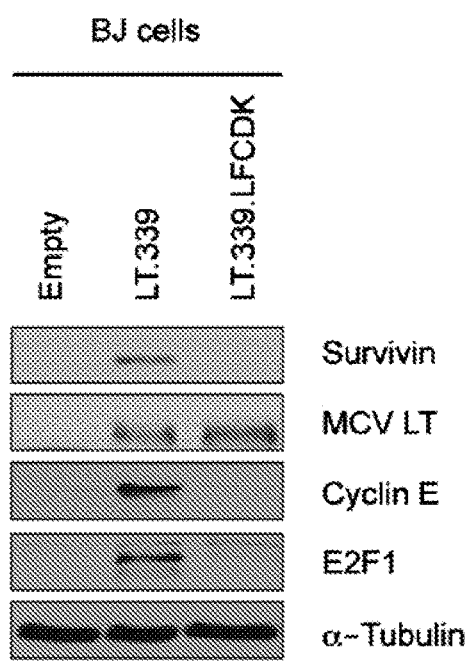
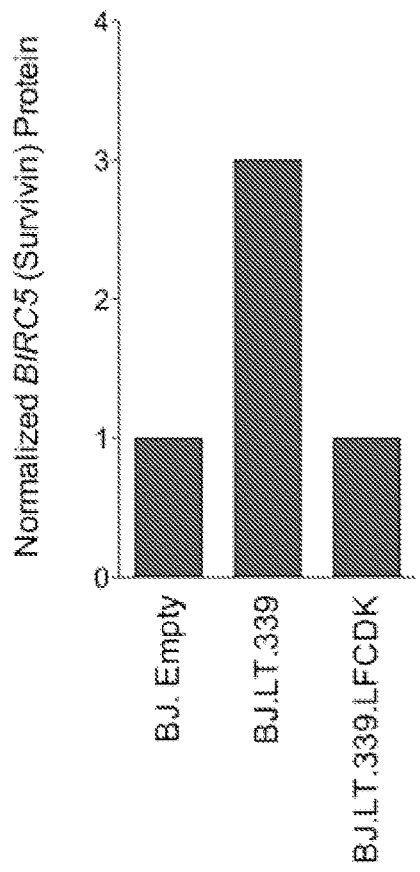
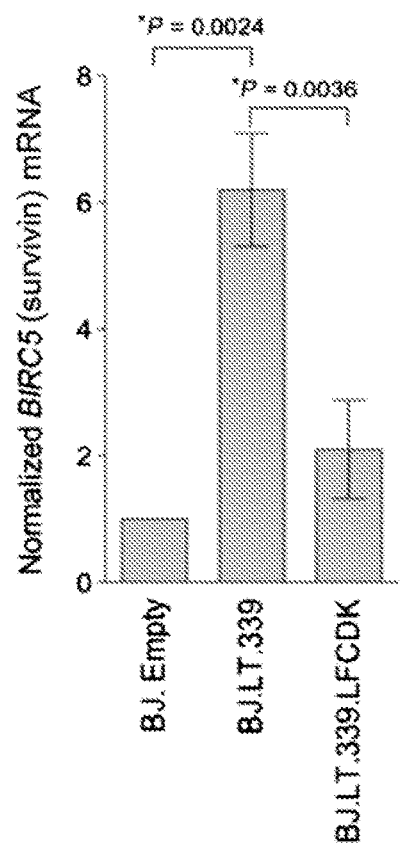
Fig. 2A
Fig. 2B                Fig. 2C

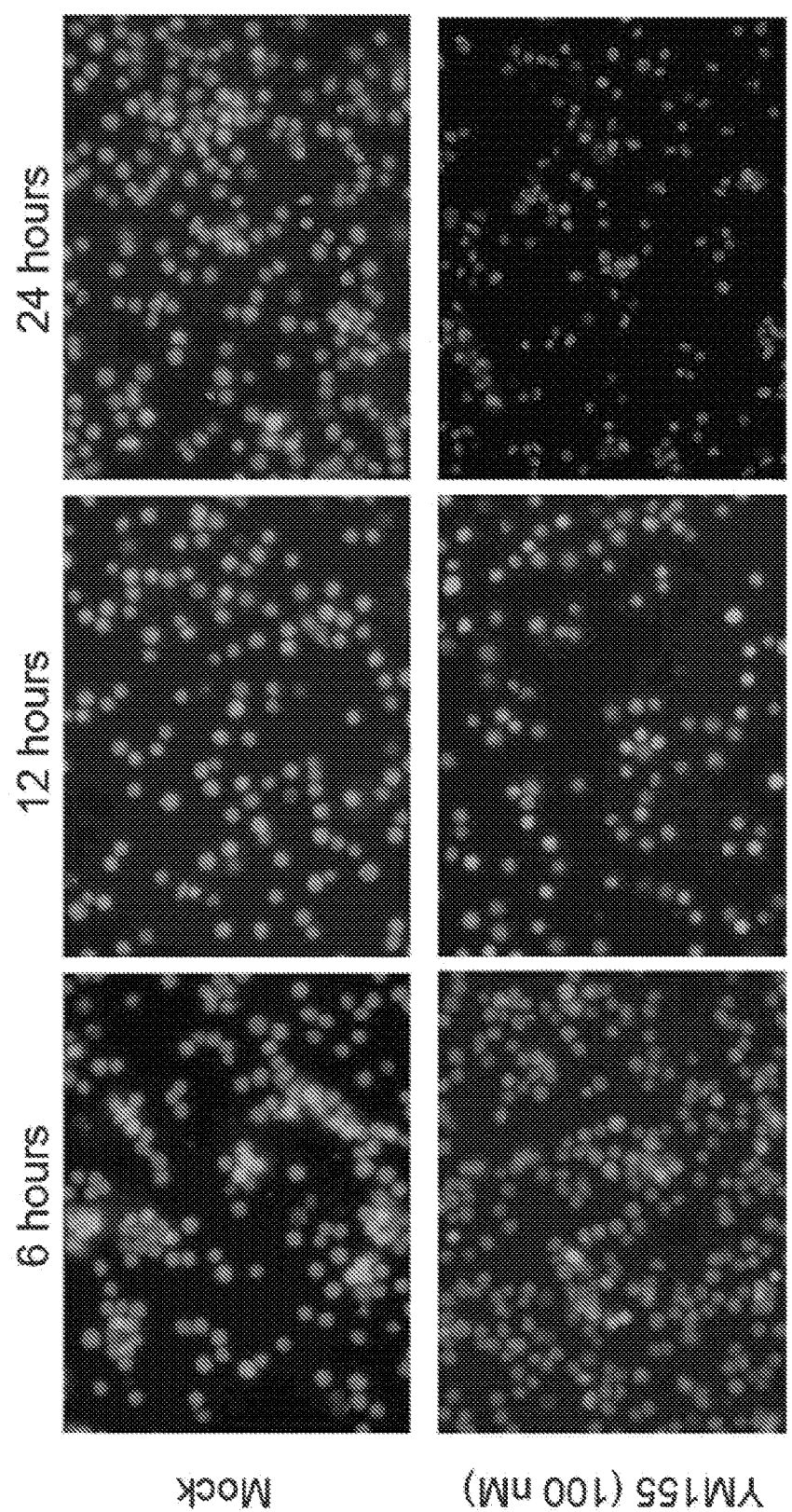

H&E

MCV LT

CK20

| Cell line | Number of mice | Treatment | Day of termination | | | Tumor Volume day 19 (mm^3) | | |
|---|---|---|---|---|---|---|---|---|
| | | | Average | Median | Range | Average | Median | Range |
| MS-1 | 5 | Saline | 34.6 | 34 | 26 -36 | 698.11 | 825 | 126-1080 |
| | 6 | YM155 | 37 | 37.5 | 24 - 44 | 380.02 | 352 | 171-600 |
| UISO | 5 | Saline | 52.4 | 47 | 37 - 81 | 122.5 | 24.5 | 13.5-486 |
| | 5 | YM155 | 53 | 54 | 41 -58 | 11.9 | 13.5 | 4-24.5 |

SEQUENCE LISTING

```
<160> NUMBER OF SEQ ID NOS: 6

<210> SEQ ID NO 1
<211> LENGTH: 58
<212> TYPE: DNA
<213> ORGANISM: Artificial Sequence
<220> FEATURE:
<223> OTHER INFORMATION: MCV T antigen shRNA

<400> SEQUENCE: 1
ccggccgcat ctctacattc aagaactcga gttcttgaat gtagagatgc ggttttg        58

<210> SEQ ID NO 2
<211> LENGTH: 58
<212> TYPE: DNA
<213> ORGANISM: Artificial Sequence
<220> FEATURE:
<223> OTHER INFORMATION: MCV T antigen shRNA

<400> SEQUENCE: 2 ccggccttc tgtcaagaag cagttctcga gaactgcttc ttgacagaaa ggttttg        58

<210> SEQ ID NO 3
<211> LENGTH: 17
<212> TYPE: DNA
<213> ORGANISM: Artificial Sequence
<220> FEATURE:
<223> OTHER INFORMATION: forward survivin primer

<400> SEQUENCE: 3
ctgcctggca gcccttt        17

<210> SEQ ID NO 4
<211> LENGTH: 20
<212> TYPE: DNA
<213> ORGANISM: Artificial Sequence
<220> FEATURE:
<223> OTHER INFORMATION: reverse survivin primer

<400> SEQUENCE: 4
cctccaagaa gggccagttc        20

<210> SEQ ID NO 5
<211> LENGTH: 20
<212> TYPE: DNA
<213> ORGANISM: Artificial Sequence
<220> FEATURE:
<223> OTHER INFORMATION: forward beta-actin primer

<400> SEQUENCE: 5
cactggctcg tgtgacaagg        20

<210> SEQ ID NO 6
<211> LENGTH: 24
<212> TYPE: DNA
<213> ORGANISM: Artificial Sequence
```

```
<220> FEATURE:
<223> OTHER INFORMATION: reverse beta-actin primer

<400> SEQUENCE: 6
cagacctact gtgcgcctac ttaa                                              24
```

USE OF SURVIVIN ANTAGONISTS IN POLYOMAVIRUS-RELATED DISEASE

CROSS-REFERENCE TO RELATED APPLICATIONS

This application is the United States national phase of International Application No. PCT/US2013/033836 filed Mar. 26, 2013, and claims priority to U.S. Provisional Patent Application No. 61/615,546 filed Mar. 26, 2012, the disclosures of which are hereby incorporated in their entirety by reference.

STATEMENT REGARDING FEDERALLY SPONSORED RESEARCH

This work was supported by National Institutes of Health Grant CA120726 and CA136363. The United States government has certain rights in the invention.

The Sequence Listing associated with this application is filed in electronic format via EFS-Web and is hereby incorporated by reference into the specification in its entirety. The name of the text file containing the Sequence Listing is 130790_ST25.txt. The size of the text file is 1,507 bytes, and the text file was created on Mar. 23, 2013.

BACKGROUND OF THE INVENTION

Field of the Invention

The present invention relates to treatments for cancer. More particularly, the present invention relates to methods for treating polyomavirus-positive cancers, such as Merkel cell polyomavirus-positive Merkel cell carcinoma.

Description of Related Art

Merkel cell carcinoma (MCC) is an aggressive cutaneous neoplasm presently treated by wide surgical excision with or without adjuvant radiation therapy. No defined chemotherapeutic regimen has proven effective, and those drug combinations in use are frequently based on MCC's histologic similarity to small cell lung carcinoma. Data from the Surveillance, Epidemiology, and End Results Program (SEER) of the National Cancer Institute indicates that MCC incidence has tripled from 0.15 in 1986 to 0.6 per 100,000 in 2006 resulting in approximately 1,500 new cases per year in the United States alone. MCC is a cancer of elderly (>65 years of age) and immunosuppressed populations that may be triggered by UV or ionizing radiation exposure. Given that these populations are increasing in developed countries, it is likely that MCC incidence will increase in coming years.

Merkel cell polyomavirus (MCV) was discovered in 2008 using digital transcriptome subtraction (DTS) during a directed search for the viral cause for MCC. Seven new human polyomaviruses have been described since 2007 using genomic technologies although MCV is currently the only polyomavirus so far established to be a cause for human cancer. DTS is a deep sequence-based method based on generation of high-fidelity (Hi-Fi) sequence datasets from tumor and control sample cDNAs. Known human cellular transcript sequences are "subtracted" from the HiFi dataset, leaving candidate sequences that might belong to a novel viral cDNA. DTS can also be used to quantitate relative cellular gene expression. MCV, similar to other polyomaviruses, is a double-stranded DNA virus that normally replicates as an episomal viral infection. MCV positive-MCC tumors are characterized by two distinct viral mutations: MCV genome integration into the human Merkel cell genome and truncation mutation of the MCV large tumor (LT) antigen gene. These mutations eliminate virus replication but leave the virus's tumor suppressor targeting domains intact. An additional important risk factor for MCC is loss of host immune surveillance, as occurs in AIDS, transplantation or aging, so that virus-positive tumor cells are not cleaved by an immune response. MCV is a common infection of human skin and MCV-positive MCCs represent an intriguing human tumor model in which mutations to the genome of a commensal virus, rather than the host genome, are required for the initiation of an aggressive cancer.

As with other polyomaviruses, differentially spliced LT and small T (sT) oncoproteins are expressed from the MCV T antigen early locus. MCV LT binds to transcriptional repressor retinoblastoma protein (RB1) family members through an N-terminal LXCXE motif that is not affected by MCV tumor-specific mutations. For SV40 polyomavirus, LT binding to RB1 with subsequent release of active E2F transcription factors is postulated to promote synthesis of genes required for entry into the S phase of the cell cycle. Cyclin E and E2F1 are positively regulated by E2F signaling and promote intracellular conditions for active DNA synthesis. SV40 LT also binds to and inhibits the pro-apoptotic tumor suppressor protein p53, but there is currently no evidence that MCV LT directly targets p53 in tumors since this corresponding region is deleted by tumor specific mutations. Other pro-survival pathways that might be targeted by MCV, such as the survivin oncoprotein, which is also regulated by RB1 signaling, had not been investigated. MCV sT, which is unaffected by tumor-specific mutations, transforms cells and activates cap-dependent translation by targeting the translation regulator 4E-BP1. When sT alone is knocked down, MCV-positive cells undergo cell cycle arrest whereas knockdown of both sT and LT together causes necroptotic cell death. Thus, both LT and sT oncoproteins are likely to contribute to the transformed phenotype of Merkel cell cancer.

Despite the growing knowledge of polyomaviruses and cancers caused by polyomaviruses, as well as a growing knowledge of the role of survivin in cancer proliferation, there is a dearth of treatments for cancers which are polyomavirus (+) and in which survivin is upregulated. Accordingly, there is a need in the art for treatments for polyomavirus (+) cancers in which survivin is upregulated.

SUMMARY OF THE INVENTION

Described herein are methods of treating or inhibiting growth of a polyomavirus (+) cancer in which survivin is upregulated. To this end, a method of treating a polyomavirus (+) cancer in which survivin is upregulated in a patient is provided. The method comprises administering to the patient a therapeutically effective amount of a composition that downregulates survivin expression or function in cells of the polyomavirus (+) cancer. The polyomavirus (+) cancer is a Merkel cell polyomavirus (+) Merkel cell carcinoma and the composition comprises YM155 in one embodiment. In another embodiment, the polyomavirus (+) cancer is a polyomavirus (+) Merkel cell carcinoma, such as a Merkel cell polyomavirus (+) Merkel cell carcinoma. The composition, according to certain embodiments includes a 1-(2-methoxyethyl)-2-methyl-4,9-dioxo-3-(pyrazin-2-ylmethyl)-4,9-dihydro-1H-naphtho[2,3-d]imidazol-3-ium (sepantronium) salt having the structure:

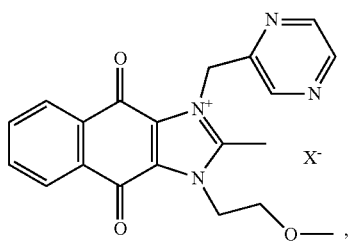

wherein X is a pharmaceutically acceptable counterion.

An example of a 1-(2-methoxyethyl)-2-methyl-4,9-dioxo-3-(pyrazin-2-ylmethyl)-4,9-dihydro-1H-naphtho[2,3-d]imidazol-3-ium salt is YM155. Alternately or in addition to the above, composition comprises one or more additional active agents, such as, without limitation one or more additional active agent is one or more of an anticancer chemotherapeutic agent, an antibiotic, a protein-based therapeutic, an antibody or fragment thereof, an antiemetic, a cell-based therapeutic, a cell-based immunotherapeutic, or a vector comprising a gene for producing a therapeutic or immunotherapeutic composition.

In yet another embodiment, the composition comprises an interfering nucleic acid, such as an interfering RNA such as siRNA or hnRNA. According to certain embodiments, the interfering nucleic acid targets one of survivin, ILF3, p54nrb or polyomavirus T antigen.

The compositions described herein is administered in a therapeutic amount or an amount or concentration to reduce or inhibit cell growth. According to one non-limiting embodiment, the composition is administered to a patient in an amount of from 0.1 mg/kg and about 5 g/kg per day for a time period ranging from one day to one year, including any increment therebetween, or alternately between about 0.1 mg/m$^2$/d and about 5 mg/m$^2$/d, such as about 2 mg/kg per day to about 10 mg/kg per day, in increments therebetween or in other increments disclosed herein or equivalents thereof, e.g., in mg/kg. According to one non-limiting embodiment, the composition is administered on from one to seven days weekly, for example and without limitation, administering YM155 to the patient in an amount of about 2 mg/kg about five times weekly to the patient.

A method of reducing growth of polyomavirus (+) cancer cells in which survivin is up-regulated is also provided. The method comprises contacting the cells with an amount of a composition that downregulates survivin expression or function effective to reduce growth of the cells. In one embodiment, the composition comprises YM155. The cells can be any polyomavirus (+) cancer cells as described herein, such as Merkel cell polyomavirus (+) Merkel cell carcinoma. The method may be performed in vitro or in vivo. The amount of any active agent used in this method may be in any range described herein and dosage is, according to certain embodiments, in a range as described herein, or its in vitro equivalent.

Also provided is a 1-(2-methoxyethyl)-2-methyl-4,9-dioxo-3-(pyrazin-2-ylmethyl)-4,9-dihydro-1H-naphtho[2,3-d] imidazol-3-ium (sepantronium) salt, for use in treating a polyomavirus (+) cancer in which survivin is up-regulated or for reducing growth of cells of a polyomavirus (+) cancer in which survivin is up-regulated. According to one non-limiting embodiment, the salt is YM155. According to another non-hinting embodiment, the polyomavirus is Merkel cell polyomavirus. In yet another non-limiting embodiment, the cancer is Merkel cell polyomavirus (+) Merkel cell carcinoma and the salt is YM155.

DESCRIPTION OF THE INVENTION

Figure 1A:
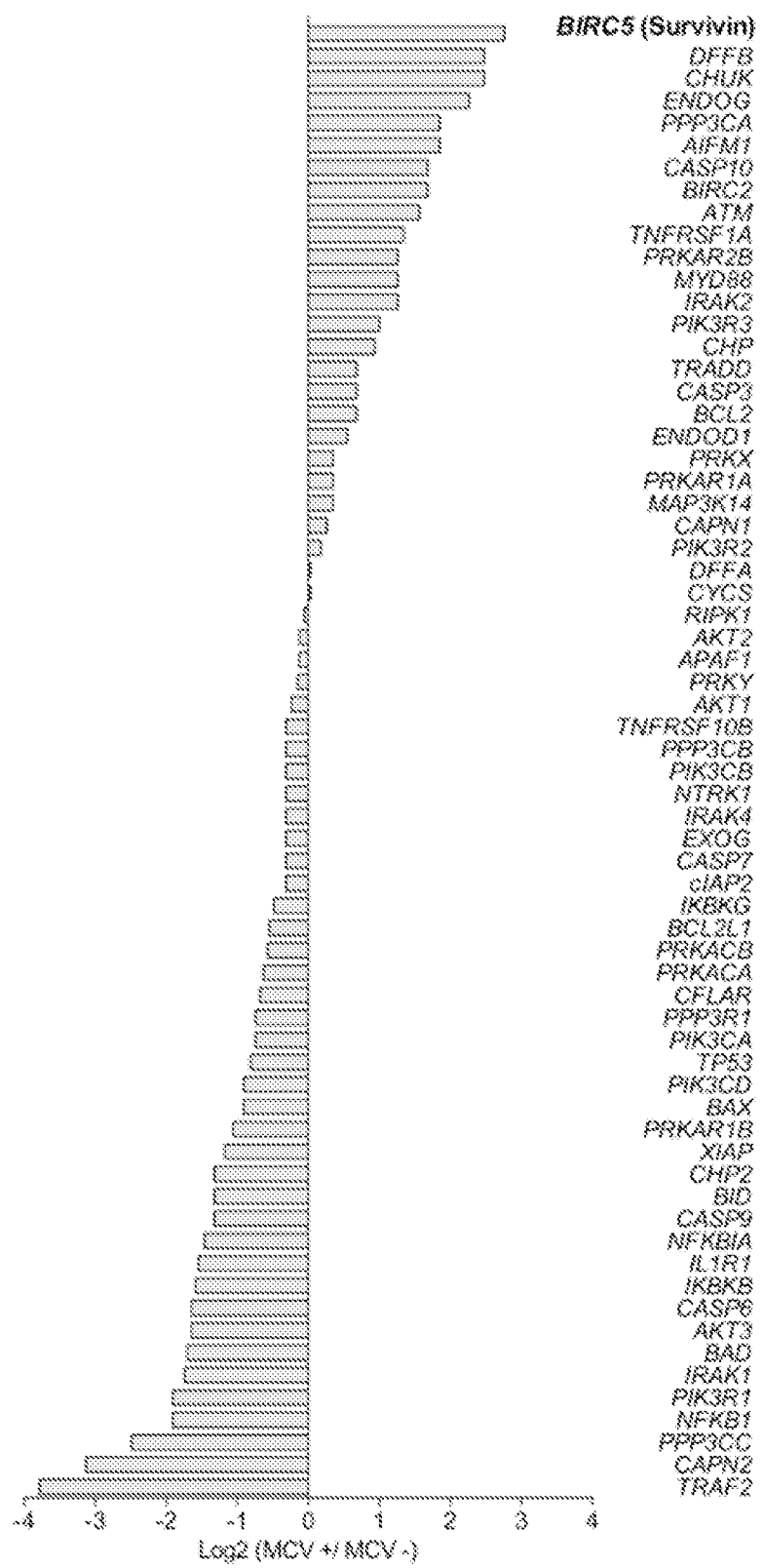
FIG. 1—Survivin oncoprotein mRNA expression is increased in MCV-positive MCC: (A) DTS comparison of 64 genes involved in programmed cell death and cell cycle regulation, showing that survivin (BIRC5) mRNA transcripts (highlighted in bold) were seven-fold higher in a MCV-positive than an MCV-negative MCC DTS cDNA library. The relative expression of genes was normalized to total sequence reads for each MCC library; (B) MCV T antigen increases survivin expression. Lentiviral MCV T antigen exon1 knockdown (panT1) decreased survivin protein expression among four MCV-positive MCC cell lines (Top panel). shCntrl is a scrambled shRNA control lentivirus. No consistent changes in XIAP, BCL-2, Bax or p53 protein levels are seen after MCV T antigen knockdown among MCC cell lines (Bottom panel). MKL-1, MKL-2, MS-1 and WaGa are MCV positive and UISO is MCV negative; (C) MCV T antigen increases survivin transcription. Survivin mRNA levels were reduced in MKL-1 but not UISO cells after T antigen knockdown indicating that T antigen acts survivin transcription. Survivin mRNA was measured by qRT-PCR and normalized to β-actin mRNA. The experiments were performed in triplicate and repeated two times (mean±SEM); (D) Survivin expression is required for MCV-positive MCC cell survival. Survivin was targeted for knock down with two shRNA lentiviral vectors, shsur1 and shsur2 in MKL-1 cells and UISO cells. MKL-1 cells initiate apoptosis after survivin knockdown, with increased expression of cleaved polyADP ribose polymerase (cPARP) and caspase 3 (cCasp3), whereas UISO cells are resistant to survivin knock down-induced apoptosis. Tubulin is used as a loading control.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases.

As used herein, the terms "comprising," "comprise" or "comprised," and variations thereof, are meant to be open ended. The terms "a" and "an" are intended to refer to one or more.

As used herein, the term "patient" or "subject" refers to members of the animal kingdom including but not limited to human beings and "mammal" refers to all mammals, including, but not limited to human beings.

Unless indicated otherwise all nucleotide sequences are provided in 5' to 3' orientation and all amino acid sequences are provided in N-terminal to C-terminal orientation.

Provided herein are methods of treating polyomavirus (+) cancers in which survivin is upregulated. Also provided herein is a method of reducing growth of polyomavirus (+) cancer cells in which survivin is up-regulated, comprising contacting the cells with an amount of a composition that downregulates survivin expression or function effective to reduce growth of the cells. Further, a 1-(2-methoxyethyl)-2-methyl-4,9-dioxo-3-(pyrazin-2-ylmethyl)-4,9-dihydro-1H-naphtho[2,3-d]imidazol-3-ium (sepantronium) salt is provided for use in treating a polyomavirus (+) cancer in which survivin is up-regulated. As used herein, "a polyomavirus (+) cancer" includes any uncontrolled growth of cells wherein the cells are positive for a polyomavirus (e.g., positive for a polyomavirus sequence). "Survivin upregulation" or "a cancer in which survivin is upregulated" means any uncontrolled growth of cells in which survivin (also known as baculoviral inhibitor of apoptosis repeat-containing 5 (BIRC5), API4, or EPR-1) is expressed at a significantly higher level (e.g., statistically significant) than in a non-survivin upregulated cancer or in noncancerous cells, and/or at a clinically significant level as compared to a non-survivin upregulated cancer or noncancerous cells Likewise "downregulation" of expression or function is a lowering of expression or function to any relevant degree, e.g., to a statistically significant degree.

Polyomavirus includes members of the family Polyomaviridae, including those in the genii *orthopolyoinavirus*, *wukipolyomavirus*, and *avipolyomavirus*. Polyomaviruses known to infect humans include JC virus (JCV), BK virus (BKV), Karolinska institute virus (KIV), Washington University virus (WUV), and Merkel cell polyomoavirus (MCV). However, the methods provided herein should be understood by one of skill in the art to be effective in treatment of any polyomavirus (+) cancer in which survivin is upregulated.

Survivin is an inhibitor of apoptosis. It inhibits caspase activation, thereby preventing apoptosis from occurring. In cancers, this can result in uncontrolled growth of cells. Survivin is not known to be expressed in terminally differentiated cells. While increased survivin expression may be associated with tumor cells and various cancers, not all cancers exhibit upregulation of surviving.

Compounds useful in treating polyomavirus (+) cancers in which survivin is upregulated include any composition capable of down-regulating or reducing survivin expression and/or function in a polyomavirus (+) cancer cell in which survivin expression is up-regulated. By "expression," it is meant the overall process by which a gene is used to produce a gene product, such as an RNA or protein, and can be determined by, for example, mRNA production or by functional assays for the gene product. In non-limiting embodiments, compounds that may be useful include nucleic acids for silencing, downregulating, or lowering expression of certain genes other than survivin (collectively, an "interfering nucleic acid", e.g., interfering RNA, antisense, siRNA, shRNA, etc.). Lower expression means reducing the amount of a gene product as compared to the gene when its expression is not lowered. Nucleic acids useful for treating polyomavirus (+) cancers in which survivin is upregulated include, without limitation, small hairpin RNAs (shRNAs) that targets tumor antigen genes. For example and without limitation, shRNA lentivirus panT1 targeting MCV T antigen exon1 sequence may be used to knock down expression of MCV T antigen in Merkel cell carcinoma (MCC) cells. For further detail, see Example 1, below. In such an embodiment, knocked down expression of MCV LT antigen prevents an increase in survivin expression.

One of ordinary skill in the art will understand that MCV T antigen is but one of numerous targets for gene knockdown that may be useful in the methods described herein. Additional targets for gene silencing or knockdown include ILF3 (Interleukin enhancer binding Factor 3, see, Yamauchi et al., Sepantronium bromide (YM155) induces disruption of the ILF3/p54(nrb) complex, which is required for survivin expression, *Biochem Biophys Res Commun.* 2012 Sep. 7; 425(4):711-716 and Nakamura et al., Interleukin enhancer-binding factor 3/NF110 is a target of YM155, a suppressant of survivin, *Mol Cell Proteomics.* 2012 July; 11(7): M111.013243). Non-limiting examples of interfering nucleic acids for silencing ILF3 are commercially available, for example shRNAs for silencing ILF3 are available from VECTOR BIOLABS of Philadelphia, Pa., and small interfering RNAs (siRNAs) are sold by ORIGENE of Rockville Md. Interfereing nucleic acids for silencing p54$^{nrb}$ also are available commercially, for example siRNA, shRNA plasmid, and shRNA lentiviral particles are sold by SANTA-CRUZ BIOTECH, INC. of Dallas, Tex. The use of these shRNAs and siRNAs to knockdown genes necessary for survivin expression is within the skill of one in the art, and use of the same falls within the spirit and scope of the present disclosure.

In other embodiments, antisense, shRNAs and siRNAs may be used to knock down expression of survivin directly. One of skill in the art is knowledgeable with the tools available, such as the availability of shRNA and siRNA for survivin. For example, SANTA CRUZ BIOTECHNOLOGY, INC. sells survivin siRNA, shRNA plasmid, and shRNA lentiviral particles. One of skill in the art is well aware of the availability of such interfering (e.g., silencing) nucleic acids, and could use such nucleic acids within the spirit and scope of the present disclosure.

Additional compounds useful for the treatment of polyomavirus (+) cancers in which survivin is upregulated are compounds that downregulate survivin expression. Non-limiting examples of such compounds include celecoxib, dimethyl-celecoxib, and mithrimycin A. These examples are to be considered exemplary and non-limiting, one of skill in the art would understand that any composition that downregulates or inhibits survivin expression may be useful in the methods of the present invention.

Other compounds for use in the treatment of polyomavirus (+) cancers in which survivin is upregulated include compounds or compositions, such as fused imidazolium derivatives, e.g., a 4,9-dioxonaphtho[2,3-d]imidazolium compound, disclosed in United States Patent Publication Nos. 2003114508 and 20060223831, both of which are incorporated herein by reference for their technical disclosure (See, also, European Patent Application Publication Nos. EP 1256576 and EP 1614686). Included in the category of useful small molecules is the sepantronium salt, 1-(2-methoxyethyl)-2-methyl-4,9-dioxo-3-(pyrazin-2-ylmethyl)-4,9-dihydro-1H-naphtho[2,3-d]imidazol-3-ium salt, having the following structure:

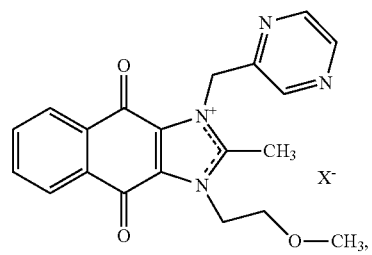

in which X is a pharmaceutically acceptable counterion. The imidazole ring is tautomeric, such that the either of the nitrogen atoms in that ring may be positively charged.

In nonlimiting embodiments, the X⁻ in the above-identified general structure is a bromide, and thus the structure is as follows:

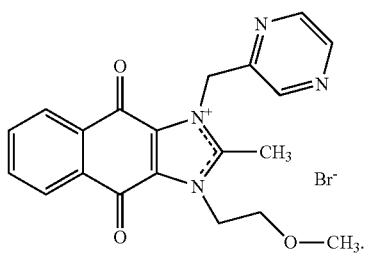

The above-identified structure is 1-(2-methoxyethyl)-2-methyl-4,9-dioxo-3-(pyrazin-2-ylmethyl)-4,9-dihydro-1H-naphtho[2,3-d]imidazol-3-ium bromide, also referred to as YM155. The imidazole ring is tautomeric, such that the either of the nitrogen atoms in that ring may be positively charged. Additional pharmaceutical salts are disclosed in United States Patent Publication Nos. 2003114508 and 20060223831 and European Patent Application Publication Nos. EP 1256576 and 1614686.

Without wishing to be bound by the theory, it is believed that YM155 functions to knockdown survivin by binding to the transcription factor interleukin enhancer-binding factor 3 (ILF3). This transcription factor normally binds to p54$^{nrb}$ to form a complex, which binds the survivin promoter to promote transcription of the survivin gene. However, it is believed that YM155 binds the ILF3-p54$^{nrb}$ complex and prevents that complex from binding the survivin promoter. Yamauchi et al. Sepantronium bromide (YM155) induces disruption of the ILF3/p54$^{nrb}$ complex, which is required for survivin expression. *Biochem Biophys Res Comm* 2012; 425: 711-716. YM155 has been evaluated for safety and efficacy in terms of other cancers, such as prostate cancer and although safe, efficacy results are mixed (See, e.g., Lewis et al., A multi-center phase II evaluation of the small molecule surviving suppressor YM155 in patients with unresectable stage III or IV melanoma, *Invest. New Drugs* (2011 29:161-166 and Tolcher et al., Phase I and pharmacokinetic study of YM155, a small-molecule inhibitor off survivin (2008) *J. Clin. Oncology* 26(32):5198-5203).

Pharmaceutically acceptable salts of any of the compounds described herein also may be used in the methods described herein. Pharmaceutically acceptable salt forms, e.g. an ionic form of a compound and its counterion, may be prepared by conventional methods known in the pharmaceutical arts, and include as a class veterinarily acceptable salts. For example and without limitation, where a compound comprises a carboxylic acid group, a suitable salt thereof may be formed by reacting the compound with an appropriate base to provide the corresponding base addition salt. Non-limiting examples include: alkali metal hydroxides, such as potassium hydroxide, sodium hydroxide and lithium hydroxide; alkaline earth metal hydroxides, such as barium hydroxide and calcium hydroxide; alkali metal alkoxides, such as potassium ethanolate and sodium propanolate; and various organic bases such as piperidine, diethanolamine, and N-methylglutamine.

Acid and base addition salts may be prepared by contacting the free base form with a sufficient amount of a desired acid or base to produce the salt in a manner known in the art. The free base may be regenerated by contacting the salt form with a base or acid (depending on the nature of the salt) and isolating the free base. The free base forms differ from their respective salt forms somewhat in certain physical properties such as solubility in polar solvents, but otherwise the salts are equivalent to their respective free base forms for purposes described herein.

Compounds comprising basic nitrogen-containing groups may be quarternized with such agents as $C_{1-4}$ alkyl halides, such as methyl, ethyl, iso-propyl and tert-butyl chlorides, bromides and iodides; $C_{1-4}$ alkyl sulfate such as dimethyl, diethyl and diamyl sulfates; $C_{10-18}$ alkyl halides, such as decyl, dodecyl, lauryl, myristyl and stearyl chlorides, bromides and iodides; and aryl-$C_{1-4}$ alkyl halides, such as benzyl chloride and phenethyl bromide. Such salts permit the preparation of both water-soluble and oil-soluble compounds.

Non-limiting examples of pharmaceutically-acceptable base salts include: aluminum, ammonium, calcium, copper, ferric, ferrous, lithium, magnesium, manganic, manganous, potassium, sodium, and zinc salts. Salts derived from pharmaceutically acceptable organic non-toxic bases include, without limitation: salts of primary, secondary, and tertiary amines, substituted amines including naturally occurring substituted amines, cyclic amines, and basic ion exchange resins, such as arginine, betaine, caffeine, chloroprocaine, choline, N,N'-dibenzylethylenediamine (benzathine), dicyclohexylamine, diethanolamine, diethylamine, 2-diethylamino ethanol, 2-dimethylamino ethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine, and tris-(hydroxymethyl)-methylamine (tromethamine).

Acid addition salts may be prepared by treating a compound with pharmaceutically acceptable organic and inorganic acids, including, without limitation: hydrohalides, such as hydrochloride, hydrobromide, hydroiodide; other mineral acids and their corresponding salts such as sulfates, nitrates, and phosphates; alkyl- and mono-arylsulfonates, such as ethanesulfonate, toluenesulfonate, and benzenesulfonate; and other organic acids and their corresponding salts, such as acetate, tartrate, maleate, succinate, citrate, benzoate, salicylate, and ascorbate.

Non-limiting examples of pharmaceutically-acceptable acid salts include: acetate, adipate, alginate, arginate, aspartate, benzoate, besylate (benzenesulfonate), bisulfate, bisulfate, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate, galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate, and phthalate.

Multiple salts forms are also considered to be pharmaceutically-acceptable salts. Common, non-limiting examples of multiple salt forms include: bitartrate, diacetate, difumarate, dimeglumine, diphosphate, disodium, and trihydrochloride.

As such, "pharmaceutically acceptable salt" as used herein is intended to mean an active ingredient (drug) comprising a salt form of any compound as described herein. The salt form preferably confers to the improved and/or desirable pharmacokinetic/pharmodynamic properties of the compounds described herein.

The compounds that knock down, silence or otherwise reduce or inhibit survivin expression or function are useful for treatment of polyomavirus (+) cancers and cancer cells in which survivin is upregulated in a patient. In nonlimiting embodiments, the polyomavirus (+) cancers and cancer cells in which survivin is upregulated is Merkel cell polyomavirus (+)Merkel cell carcinoma and Merkel cell carcinoma cells. Merkel cell carcinoma may be classified as MCV (+) or (−).

A method of treating a polyomavirus (+) cancer in which survivin is upregulated in a patient is provided. The method comprises administering an amount of a compound effective to reduce survivin expression or function in the cancer and thereby treat the cancer in a patient. For each compounds or compositions described herein, the compounds or compositions are administered in an amount effective to treat a polyomavirus (+) cancer and/or cancer cells in which survivin is upregulated. As used herein, "treat," "treating," or "treatment" refers to administering an amount of any compound or composition described herein in amount effective to achieve any clinically-relevant end-point in a patient; including but not limited to, in the context of a cancer, reducing or decreasing cancer cell growth rates, reducing or decreasing tumor growth or size, and/or amelioration of one or more clinical symptoms of the cancer in a patient.

An effective dose or dose range is expected to vary for the compounds described herein for any number of reasons, including the molecular weight of the compound, bioavailability in the dosage form, route of administration, solubility of the compound in a given excipient (e.g., carrier or vehicle), specific activity (e.g., $EC_{50}$), etc. In any case, the effective range (e.g., the therapeutic window) between the minimally-effective dose, and maximum tolerable dose in a patient can be determined empirically by a person of skill in the art, with end points being determinable by in vitro and in vivo assays, such as those described herein and/or are acceptable in the pharmaceutical and medical arts for obtaining such information regarding agents, such as parenteral and/or intravenous compositions. Different concentrations of the agents described herein are expected to achieve similar results. The compounds can be administered one or more times daily, for example two to four times daily, once every two, three, four, five or more days, weekly, monthly, etc., including increments therebetween. It is possible to deliver the drug continuously, for instance in severe cases, or substantially continuously. A composition can be administered for a duration effective to treat a cancer in a patient, such as until a patient is deemed cancer-free, or for a length of time suitable to treat an ordinary patient. A person of ordinary skill in the pharmaceutical and medical arts will appreciate that it will be a matter of design choice and/or optimization to identify a suitable dosage regimen for improving symptoms of a condition.

In non-limiting embodiments, the composition, for example and without limitation, YM155 is administered parenterally to a MCC patient in an effective dosage range between about 0.1 mg/kg and about 5 g/kg per day, or an equivalent thereof, for a time period ranging from one day to one year, including any increment therebetween, or alternately between about 0.1 mg/m²/d and about 5 mg/m²/d. In embodiments in which the composition is administered continuously, for example intravenously, an exemplary effective range for YM155 is between about 0.5 or 1 mg/m²/d and about 10 mg/m²/d, 1.8-6.0 mg/m²/d, including 4.8 mg/m²/d and 1, 2, 3, 4, 5, 6, 7, 8, 9 and 10 mg/m²/d.

Any of the compounds described herein may be compounded or otherwise manufactured into a suitable composition for use, such as a pharmaceutical dosage form or drug product in which the compound is an active ingredient. Compositions may comprise a pharmaceutically acceptable carrier, vehicle or excipient. An excipient is an inactive substance used as a carrier or vehicle for the active ingredients of a medication. Although "inactive," excipients may facilitate and aid in increasing the delivery, stability or bioavailability of an active ingredient in a drug product. Non-limiting examples of useful excipients for parenteral dosage forms include: rheology modifiers, emulsifiers, oils, adjuvants, buffers, salts, acids, bases, diluents, solvents, preservatives, antioxidants, sorbents, vitamins, etc., as are available in the pharmaceutical/compounding arts. In non-limiting embodiments, the dosage form is any dosage form suitable for parenteral or intravenous administration and the composition comprises water, saline (e.g., normal saline, 0.9% w/v NaCl in water), phosphate-buffered saline and other buffered solutions, dextrose, emulsifiers etc., as are broadly known in the pharmaceutical arts. Therapeutic/pharmaceutical compositions are prepared in accordance with acceptable pharmaceutical procedures and practices, such as are described in *Remington: The Science and Practice of Pharmacy,* 21st edition, Eds. Paul Beringer et al., Lippincott, Williams & Wilkins, Baltimore, Md. Easton, Pa. (2005), describing a variety of formulations useful in the methods described herein, such as parenteral and intravenous dosage forms.

In another embodiment any compound as described herein is provided and delivered in a transdermal device. Suitable structures and compositions for such a device are well-known in the pharmaceutical arts, generally including an occluding backing comprising an adhesive on one side to face a patient, and a drug reservoir on the same side of the occluding backing as the adhesive. The reservoir may be a non-woven fabric or gauze, or a hydrogel in which an active agent, such as any composition described herein may be absorbed or admixed. Often a permeation enhancing compound is includes in the reservoir to facilitate transfer of the active agent into/through the skin. See, e.g., *Remington: The Science and Practice of Pharmacy,* 21st edition, Eds. Paul Beringer et al., Lippincott, Williams & Wilkins, Baltimore, Md. Easton, Pa. (2005). One non-limiting example of a transdermal device is a microneedle array, such as is disclosed in United States Patent Publication No. 20110098651, incorporated herein by reference.

Additional compounds or compositions may be included in a drug product comprising one or more of the compounds for reducing survivin expression and/or function described above. In one embodiment, an additional active agent (drug), that is a compound having a physiological activity, such as a second anticancer chemotherapeutic drug is co-administered with or co-formulated with the compound(s) for reducing survivin expression and/or function described above (that is, in the same dosage form, such as an intravenous solution comprising more than one compound or composition). Non-limiting examples of anticancer drugs (chemotherapeutics) that may be combined with the survivin-modulating composition, such as YM155 include: carboplatin (CBDCA), cisplatin (CDDP), paclitaxel (TXL), vinorelbine (VIN), ifosfamide (IFM), gemcitabine (GEM), irinotecan (CPT-11), docetaxel (TXT), etoposide (ETP), cytarabine (ara-C), doxorubicin (DXR), dacarbazine (DTIC)

and rituximab (RTX), rituximab or combinations thereof, such as a rituximab-containing combination therapy selected from R-ICE (consisting of rituximab, ifosfamide (IFM), carboplatin and etoposide (ETP)), and R-DHAP (consisting of rituximab, cytarabine (ara-C), and cisplatin as anticancer agents). See, e.g., U.S. Pat. No. 8,003,105. Non-limiting examples of other compounds or compositions that might be combined with the compositions described herein for use in treating polyomavirus (+) cancers in which survivin is up-regulated include: antibiotics, an (second) interfering nucleic acid, analgesics, anti-inflammatories, protein-based therapeutics, such as cytokines or interleukins, antibodies of fragments thereof, an antiemetic, a cell-based therapeutic (e.g., a cell-based immunotherapeutic, such as, without limitation, an engineered dendritic cell), and/or a vector comprising a gene for producing a therapeutic (e.g, an immunotherapeutic), such as a plasmid, a recombinant viral nucleic acid or a recombinant viral transducing particle (a viral particle, such as an Adenovirus, Adeno-Associated Virus, retrovirus, etc. transducing particle, carrying a recombinant viral genome in which a desired gene has been placed, for example a transducing virus particle for delivery of an immunotherapeutic, an interfering nucleic acid or a protein-based therapeutic). See, e.g., International Patent Publication Nos. WO 2012027379 and WO2009048560, incorporated herein by reference for their technical disclosure.

EXAMPLES

Example 1

Discovery of a new cancer virus can be leveraged to rapidly identify rational anticancer therapies. MCV upregulates survivin oncoprotein transcription in MCC through its RB1-sequestering LT domain and that a survivin inhibitor selectively targets MCV-positive tumor cells. In contrast, screen of 1360 pharmacologically-active compounds failed to identify any with selective activity against MCV-positive MCC, and only a few compounds (bortezomib and topoisomerase I and II inhibitors) show pharmacologically-relevant activity against MCC cell lines. A transcriptional inhibitor of survivin (YM155) (Nakahara et al., YM155, a novel small-molecule survivin suppressant, induces regression of established human hormone-refractory prostate tumor xenografts. *Cancer Res* 67, 8014 (Sep. 1, 2007); Tolcher et al., A phase II study of YM155, a novel small-molecule suppressor of survivin, in castration-resistant taxane-pretreated prostate cancer. *Annals of Oncology* (Aug. 22, 2011)) is highly potent in inducing MCC cell death. It is cytostatic in MCC xenografts in mice and well tolerated. These findings show that basic genome investigations in cancer causation can lead to promising new therapies for an often intractable and enigmatic cancer.

Methods

Cell Culture

Seven Merkel cell carcinoma cell lines: MKL-1, MKL-2, MS-1, UISO, MCC13, MCC26 and WaGa (kind gift of Jurgen Becker (Houben et al., Merkel cell polyomavirus-infected Merkel cell carcinoma cells require expression of viral T antigens. *J Virol* 84, 7064 (July, 2010); Ronan et al., Merkel cell carcinoma: in vitro and in vivo characteristics of a new cell line. *J Am Acad Dermatol* 29, 715 (November, 1993); Rosen et al., Establishment and characterization of a neuroendocrine skin carcinoma cell line. *Lab Invest* 56, 302 (March, 1987)); NCI-H69 small cell lung cancer cell line (ATCC); 293 human embryonic kidney cells (ATCC); U2OS osteosarcoma cell line (kind gift of Ole Gjoerup); BJhTERT immortalized foreskin fibroblast cell line (kind gift of Ole Gjoerup); and BJ primary foreskin fibroblasts (ATCC) were used to screen and evaluate the small molecules examined in this study (Houben et al., *J Virol* 84, 7064 (July, 2010); Ronan et al., *J Am Acad Dermatol* 29, 715 (November, 1993); Rosen et al., *Lab Invest* 56, 302 (March, 1987)). The Merkel cell lines and NCI-H69 were grown in RPMI 1640 supplemented with 10% fetal calf serum, penicillin and streptomycin at 37° C. in humidified air containing 5% $CO_2$. The remaining cell lines were grown in DMEM supplemented with 10% fetal calf serum.

Compounds

A total of 1,360 compounds were used in the initial screening survey: 1,280 compounds from LOPAC1280 library (Sigma Aldrich, accessed through University of Pittsburgh Drug Discovery Institute), 89 compounds from NCI's Approved Oncology Drug Set II (from The NCI/DTP Open Chemical Repository, http://dtp.cancer.gov), 6 LT ATPase inhibitors (MAL2-11B, MAL3-101, MAL2-51, DMT3084, bithionol and hexachlorophene (Wright et al., Inhibition of Simian Virus 40 replication by targeting the molecular chaperone function and ATPase activity of T antigen. *Virus Res* 141, 71 (April, 2009); Seguin et al., High-Throughput Screening Identifies a Bisphenol Inhibitor of SV40 Large T Antigen ATPase Activity. *Journal of Biomolecular Screening*, (Sep. 23, 2011)) and 4 compounds that target and inhibit p53 and MDM2 binding (Nutlin-3, YH264A, Y2H265A and KK_NW_16A (Czarna et al., Robust generation of lead compounds for protein-protein interactions by computational and MCR chemistry: p53/Hdm2 antagonists. *Angewandte Chemie* 49, 5352 (Jul. 19, 2010); Popowicz et al., Structures of low molecular weight inhibitors bound to MDMX and MDM2 reveal new approaches for p53-MDMX/MDM2 antagonist drug discovery. *Cell Cycle,* 1104 (Mar. 15, 2010)). 19 compounds in common between the LOPAC 1280 and NCI Approved Oncology Drug Set II library were screened twice with comparable results. NCI Approved Oncology Drug Set II, SV40 LT ATPase inhibitors and MDM2 inhibitors were reconstituted as recommended by supplier. YM155 (4,9-Dihydro-1-(2-methoxyethyl)-2-methyl-4,9-dioxo-3-(2-pyrazinylmethyl)-1H-naphth[2,3-d]imidazolium bromide) was purchased from Active Biochemicals Co. Ltd. (Hong Kong, China). Reconstituted compounds were diluted in cell culture media to obtain a 100× stock concentration prior to addition to cells. Doxorubicin (positive control) was obtained from Sigma-Aldrich and DMSO (negative control) was obtained from Fisher Bioreagents.

For $EC_{50}$ measurements, dose-response curves were established for 17 drugs obtained individually in bulk stocks. Iodoacetamide (I1149), sanguarine chloride (S5890), NSC95397 (N1786), chelerythrine chloride (C2932), calmidazolium chloride (C3930), tetraethylthiuram disulfide (T1132), bay 11-7085 (B5681), quinacrine dihydro chloride (Q3251), ellipticine (E3380), amsacrine hydrochloride (A9809) and nutlin-3 (N6287) were purchased from Sigma Aldrich, USA. Mitoxantrone (NSC279836), daunorubicin HCl (NSC82151), valrubicin (NSC246131), topotecan HCl (NSC609699), teniposide (NSC122819) and bortezomib (NSC681239) were kindly provided by the NCI/DTP Open Chemical Repository.

MKL-1 Cytotoxicity Screen

MKL-1 cells were seeded at a density of 6000 cells in 50 μl of medium per well (120 cells/μl) in opaque polypropylene 384-well microplates (#781080, Greiner Bio-One, Germany). Cells were incubated at 37° C. in humidified air containing 5% $CO_2$ for 24 hours. Thereafter, 25 μl of medium containing 3× drug per well was added to the plates, which were incubated for an additional 48 hours. Cell viability was measured using Cell Titer Glo (Promega) following manufacturer's instructions. The validity of Cell Titer Glo results in measuring cell viability was confirmed by trypan blue exclusion staining and WST-1 assays (Roche) in pilot studies.

The LOPAC1280 library was screened at a final concentration of 10 μM for each compound and the NCI library was screened at a final concentration of 1 μM for each compound. MAP-C (Titertek Instruments Inc) and Janus MDT (PerkinElmer Inc) were used for automated resuspension and the addition of LOPAC library drugs to assay plates. NCI library compounds were added to wells by manual pipetting.

Cell Titer Glo assays were performed in duplicate using 384 well plates, each containing 24 wells with 1% DMSO (negative control) and 32 wells with 200 μM doxorubicin (positive control). Screening results were evaluated on the basis of percentage cell survival normalized to the DMSO control (100%). Positive candidates were identified using a cut-off value of <10% cell survival. The average Z factor was 0.61 (range 0.34-0.74) for the LOPAC library screen and 0.82 for the NCI library screen (range 0.75-0.91).

Dose-Response Studies

Compounds that met the selection criteria <10% cell survival were purchased or obtained in bulk from NCI/NIH Developmental Therapeutics Program. Serial drug dilutions from $10^{-4}$ M to $10^{-9}$ M were used on MCC and non-MCC cell lines. Cells were seeded into 384-well plates at 6000 cells in 50 μl of medium per well. After 24 hours, 25 μl of 3× drugs were added at increasing concentration to each well. Cell viability was then measured using Cell Titer Glo (Promega) kit following manufacturer's instructions as described previously. Each drug concentration was tested in triplicate for each cell line and experiments were repeated twice. $EC_{50}$ doses for the drugs were calculated using a four parameter logistic equation (GraphPad Prism).

Trypan Blue Dye Exclusion Assay

Cells were equally seeded and treated with YM155 for 48 hours. To count blue stained dead cells, cells were treated with Accutase (Millipore), collected, resuspended in PBS, mixed with equal volume of Trypan blue (Lonza, 0.4%) and counted using a hemocytometer under the microscope. The counts were done in triplicate and the experiment was repeated three times.

Expression and shRNA Lentivirus Construction

To express codon optimized full-length MCV large T antigen, the gene was synthesized (DNA2.0) from the MCV-HF strain large T antigen sequence template (H. Feng et al., Cellular and viral factors regulating merkel cell polyomavirus replication. *PloS one* 6, e22468 (2011)) (GenBank ID: JF813003) and cloned into the lentiviral pLVX EF puro vector (Shuda et al., Human Merkel cell polyomavirus small T antigen is an oncoprotein targeting the 4E-BP1 translation regulator. *J of Clin Invest*, (Aug. 15, 2011)). Truncated tumor LT339 (representing the MCV339 strain, amino acid 1-455) and LT339.LFCDK were cloned by site-directed mutagenesis from the codon-optimized full-length LT into pSMPUW-hygro vector (Cell Biolabs Inc.) (Shuda et al., Human Merkel cell polyomavirus small T antigen is an oncoprotein targeting the 4E-BP1 translation regulator. *J of Clin Invest*, (Aug. 15, 2011)). Cells were infected with lentiviruses in the presence of 1-4 μg/ml polybrene for 24 hours, followed by media change. Stable selection with either puromycin (1 μg/ml) or hygromycin (200 μg/ml) was initiated 48 hours after infection.

To express survivin under a different promoter and create stable cell lines a cloned pIH survivin retrovirus was used. After infection cells were selected with 300 μg/ml for 2 weeks.

shRNA for MCV T antigen knockdown was generated and used as previously described (Houben et al., Merkel cell polyomavirus-infected Merkel cell carcinoma cells require expression of viral T antigens. *J Virol* 84, 7064 (July, 2010)), we renamed shT1 in Houben et al. to panT1. To knockdown survivin gene expression, shRNA sequence (shsur1-5' ccg-gCCGCATCTCTACATTCAAGAACTC GAGTTCTT-GAATGTAGAGATGCGGtttttg-3' (SEQ ID NO: 1) and shsur2-5' ccggCCTTTCTGT CAAGAAGCAGTTCTCGA-GAACTG CTTCTTGACAGAAAGGtttttg-3' (SEQ ID NO: 2) (Lower cased nucleotides indicate linker sequences used for cloning)) was cloned into a pLKO.1puro lentiviral vector. shCntrl is a nontargeting shRNA negative control (Houben et al., Merkel cell polyomavirus-infected Merkel cell carcinoma cells require expression of viral T antigens. *J Virol* 84, 7064 (July, 2010)). Cell harvesting was performed six days post infection.

Immunoblotting

Cells were lysed in buffer (RIPA or 10 mM Tris-HCl pH 8.0, 0.6% SDS) containing protease inhibitor cocktail (Roche). Lysates were electrophoresed in 10% SDS-PAGE, transferred to nitrocellulose membrane (Amersham) and reacted with specific antibodies (CM2B4, (1:5000 dilution) (Shuda et al., Human Merkel cell polyomavirus infection I. MCV T antigen expression in Merkel cell carcinoma, lymphoid tissues and lymphoid tumors. *Int J Cancer* 125, 1243 (Sep. 15, 2009)), cleaved PARP, cleaved caspase3, survivin, XIAP, p53, Bcl-2, Bax (1:1000 dilution, Cell Signalling Technologies), E2F1, cyclin E (1:1000 dilution, Santa Cruz Biotechnology), LC3 (1:1000 dilution, Novus Biologicals) or α-tubulin (1:5000 dilution, Sigma)) overnight at 4° C., followed by anti-mouse (1:5000 dilution, Amersham) or anti-rabbit IgG-HRP conjugates (1:3000 dilution, Cell signaling) for 1 hour at room temperature. Peroxidase activity was detected using Western Lightning plus-ECL reagent (Perkin Elmer). For quantitative immunoblotting, Odyssey Infrared Imaging system (LICOR) was used with IRDye 800-conjugated secondary antibodies (1:5000 dilution, Rockland Immuno chemicals).

qRT-PCR

RNA was extracted from cell lysates using Trizol reagent (Invitrogen) and cDNA was synthesized using SuperScript III First Strand Synthesis (Invitrogen). Quantitative real-time PCR for survivin was performed on cDNA using the SYBR green method (based on manufacturer's protocol, Applied Biosystems). Primers used were 5'-CTGCCTGCA-GCCCTTT-3' (SEQ ID NO: 3)(Forward) and 5'-CCTC-CAAGAAGGGCCAGTTC-3' (SEQ ID NO: 4) (reverse) for survivin (Nakahara et al., YM155, a novel small-molecule survivin suppressant, induces regression of established human hormone-refractory prostate tumor xenografts. *Cancer Res* 67, 8014 (Sep. 1, 2007)) and 5'-CACTGGCTC GTGTGACAAGG-3'(SEQ ID NO: 5) and 5'-CAGAC-CTACTGTGCGCCTACTTAA-3' (SEQ ID NO: 6) for β-actin. The relative change in expression was calculated using the Pffafl method (Pfaffl, A new mathematical model for relative quantification in real-time RT-PCR. *Nucleic Acids Research* 29, e45 (May 1, 2001)). Experiments were repeated six times (2 biological repeats with 3 technical replicates each).

Cell Cycle Analysis

MKL-1 cells were treated with Accutase (Millipore) to break clumps and then resuspended in fresh medium containing drug and treated for 12 hours. Three hours before harvest 10 μM Bromodeoxyuridine (BrdU) was added. Cells were then harvested and fixed in chilled 70% ethanol and left overnight. The next day cells were washed, resuspended in 200 μl of 2M HCl/Triton X (1%) and incubated for 30 mins at room temperature. Cells were then centrifuged at 2000 rpm for 10 mins and neutralized in 200 μl of 0.1M sodium tetraborate, pH 8.5 solution. Cells were then washed, suspended in 20 μl of PBS containing 0.5% tween20, 1% donkey serum and 2ul of anti-BrdU antibody (1:10 diution, BD Biosciences) and incubated overnight at 4° C. Cells were then washed and incubated with secondary antibody-anti mouse Alexa488 (1:1000) for 1 hour at room temperature. Cells were finally washed, suspended in PBS containing 100 μg/ml of RNase A, 50 μg/ml of PI (propidium iodide) and 0.05% Triton X and incubated for 30 mins at 37° C. in the dark. The cells were then subjected to FACS using the accuri C6 flow cytometer (UPCI shared resources).

Cell Death Evaluation by CFDA and PI Staining

Upon harvesting cells are resuspended in 2 ml of PBS containing 4 μg/ml PI (propidium iodide, Sigma) and 10 μM Carboxy fluorescin diacetate (CFDA, Invitrogen) at room temperature for 10 mins. Cells were then rinsed in 1× PBS and then examined under the microscope. Quantitation was done using ImageJ software.

Mouse Xenograft Studies

Compounds

For in vivo experiments, clinical-grade bortezomib (Velcade) was purchased from the University of Pittsburgh Cancer Institute Pharmacy and YM155 was purchased from Active Biochemicals Ltd. (Hong Kong, China). Compounds were dissolved in sterile 0.9% saline solution for administration to animals.

Animals

Six-week-old female triple immune-deficient NSG (Nod-SCID gamma) mice (Jackson Laboratory) were maintained in a specific pathogen-free environment.

Xenograft Drug Treatments

MCC cells were checked for viability >90% by trypan blue staining, resuspended in PBS ($2\times10^7$ cells in 100 μl) and inoculated subcutaneously into the right flank of mice. Once tumors were palpable (2-4 weeks after injection), mice were assigned sequentially into receiving either bortezomib, YM-155 or saline treatment arms.

Figures 1, 11A:
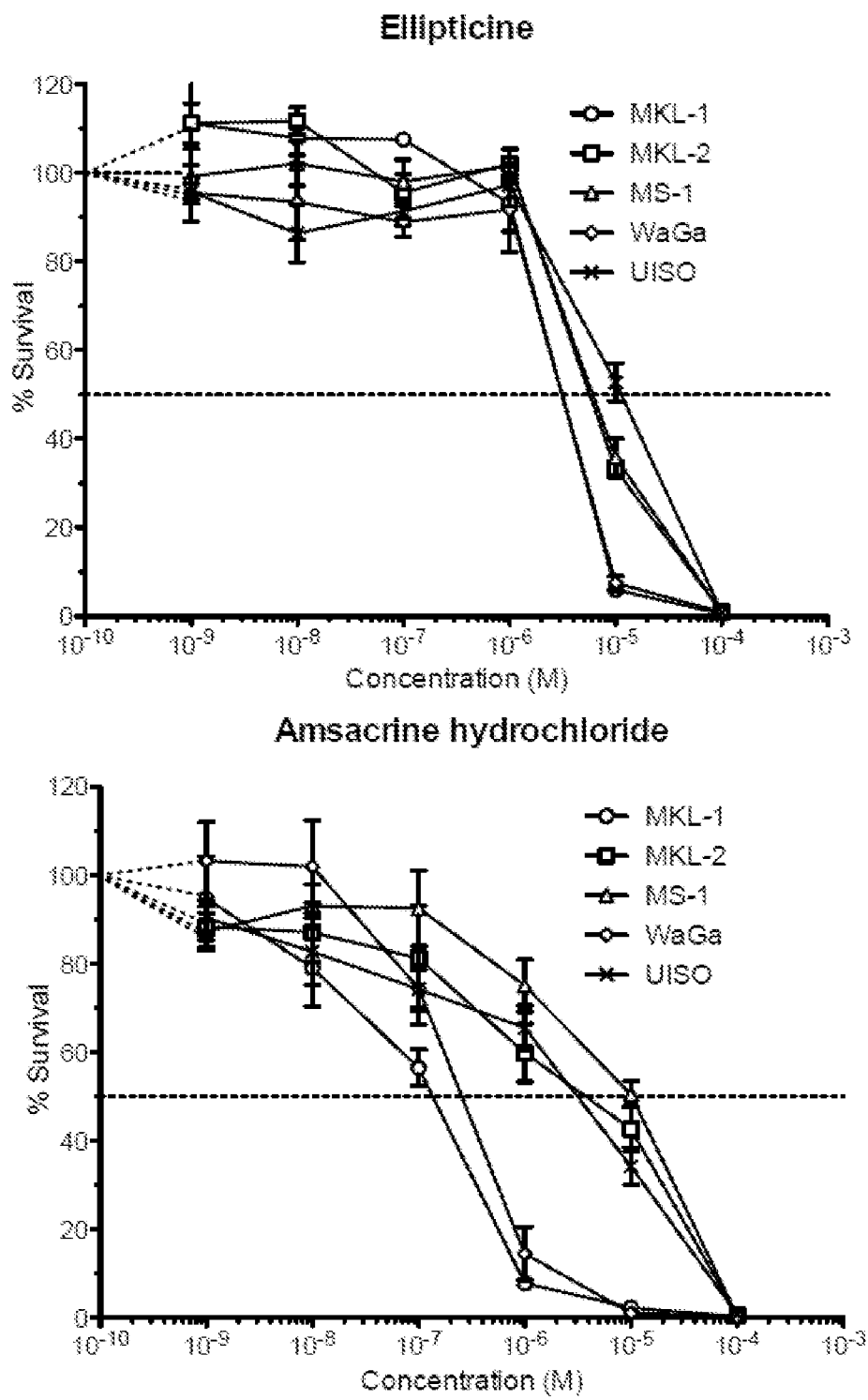
Figures 2, 11A:
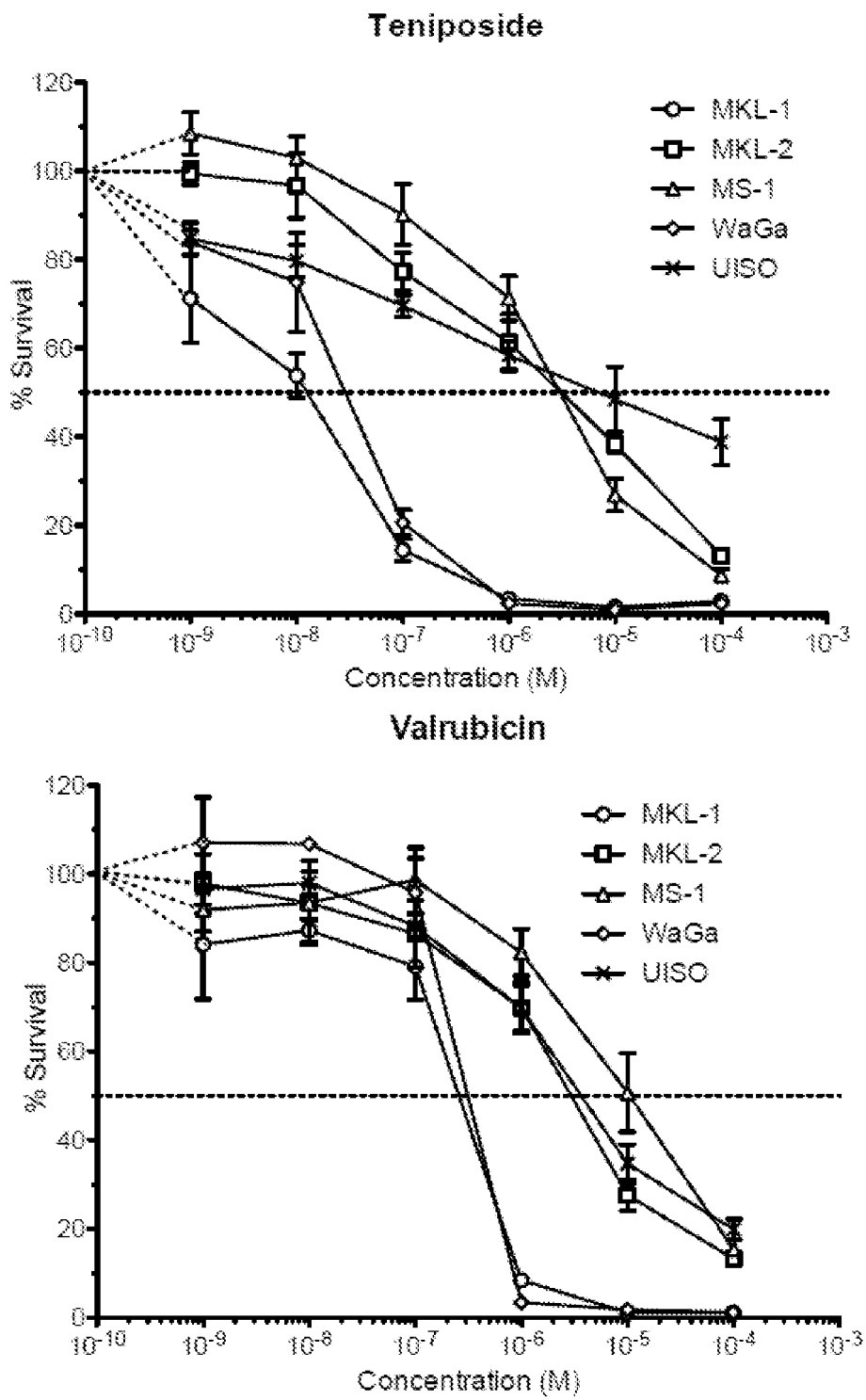
FIG. 2—MCV LT protein isoform induces survivin oncoprotein expression in human BJ cells by targeting retinoblastoma protein (RB): (A) BJ cells were transduced with either empty vector, a tumor-derived LT cDNA (LT.339) or an LT cDNA with an inactive RB binding domain (LT.339LFCDK). Immunoblotting reveals that MCV LT.339 induces survivin expression but LT.339LFCDK does not. A similar pattern is seen for other S phase cell cycle proteins such E2F1 and cyclin E that are also transcriptionally repressed by RB; (B) LICOR quantitative immunoblotting for survivin in (A), normalized to tubulin (arbitrary units); (C) Survivin mRNA levels increased in BJ cells expressing LT.339 protein but not in cells expressing the RB1 binding mutant LT.339LFCDK. BJ cells expressing either empty, LT.339 or LT.339LFCDK were serum starved for 48 hours and then harvested for RNA. Survivin mRNA was measured by qRT-PCR and normalized to β-actin mRNA. The experiments performed three times in triplicate (mean±SEM).
Figures 3, 11A:
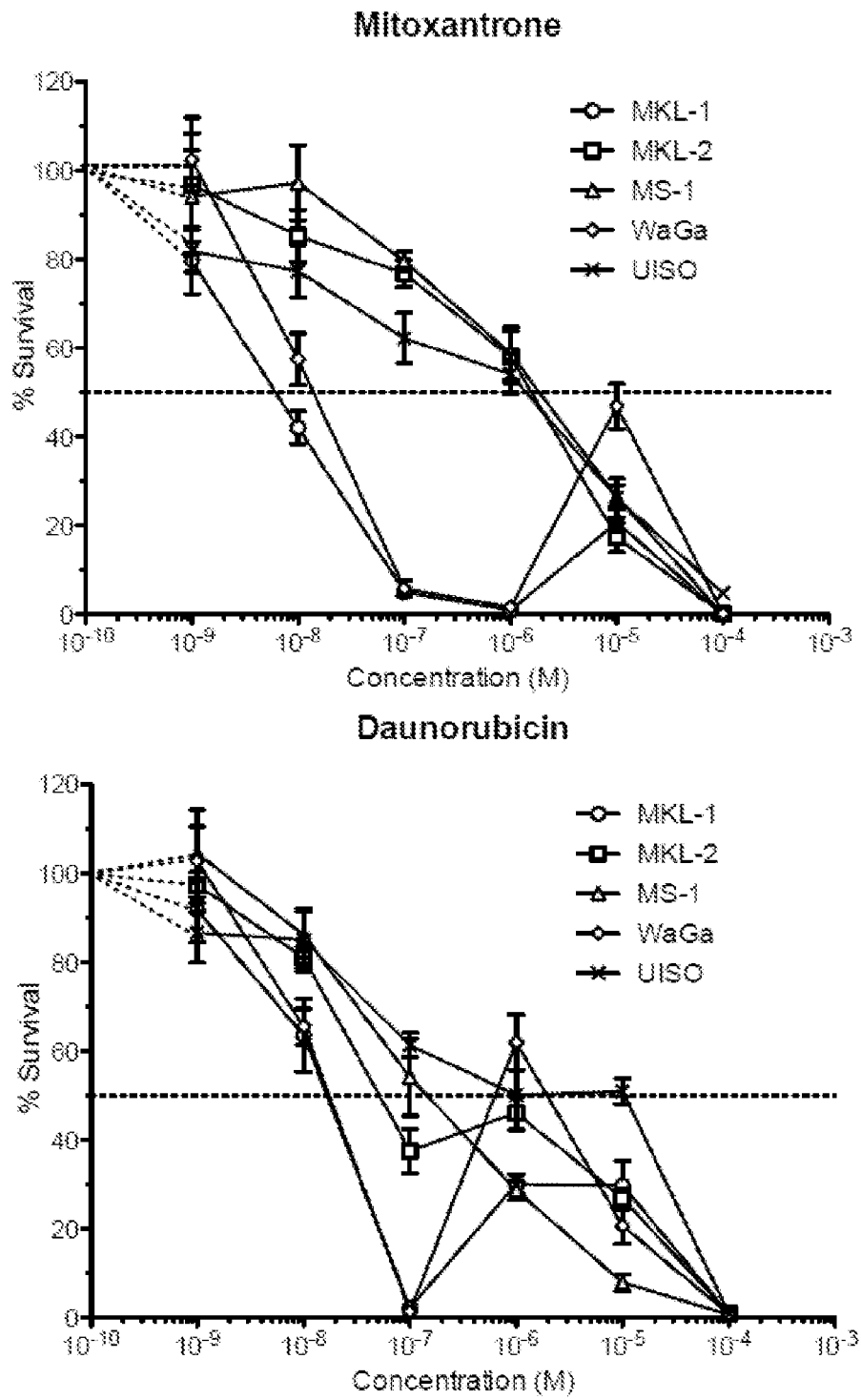

All treatments were delivered for three consecutive weeks. Bortezomib treatment was delivered subcutaneously twice weekly at 1 mg/kg per mouse. To avoid previously observed side effects, mice were given hydrogel (ClearH$_2$O) and kept at 30° C. (using a heating blanket to heat up half of the cage) during bortezomib treatment. YM-155 (2 mg/kg) was given intraperitoneally on five consecutive days, followed by a two-day treatment free interval. The control group received saline alone (21 mice on the same dosing schedule as bortezomib and 20 mice on the same dosing schedule as YM155 (FIG. 3). Day 19 was the last day of drug delivery for both schedules and hence the end of treatment. Caliper measurements of the longest perpendicular tumor diameters were performed every other day and tumor volumes were calculated using the formula: (width)$^2$×(length/2). Animals were sacrificed when tumors reached 2 cm in any dimension, >20% weight loss or when they became moribund. Survival was defined as time from the first day of treatment until death/sacrifice.

Statistical Analysis

Figure 5A:
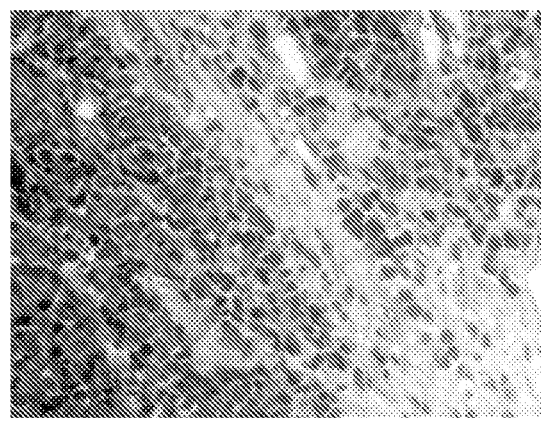
FIG. 5—YM155 inhibits growth of human MKL-1 MCC xenografts in NSG mice: (A) MKL-1 xenograft tumors stained with hematoxylin and eosin, MCV LT (CM2B4 antibody) and CK20 (magnification 40×); (B) MKL-1 xenograft survival curves after drug treatment. Mice were subcutaneously injected with 20 million MKL-1 cells and assigned to three weeks drug treatment after tumors became palpable (see text). No significant difference was found between saline and bortezomib treatment. Tumor progression was significantly delayed by YM155, with none of the YM155-treated mice dying during treatment (up to day 19) compared to 23 of 31 (74%) saline and 14 of 21 (67%) bortezomib-treated mice. Tumor progression recurred for all YM155-treated mice once treatment was stopped; (C) Piecewise linear hierarchical Bayesian model for tumor volumes in treated mice. Colored lines show estimated central population tumor volumes with shaded regions representing 95% credible intervals. Actual tumor volumes (grey lines) for each mouse are shown for comparison. YM155 treatment retards tumor growth compared to saline or bortezomib treatment; (D) Table showing day of termination and tumor volumes for MS-1 and UISO xenograft mice used in the study.
Figure 5A:
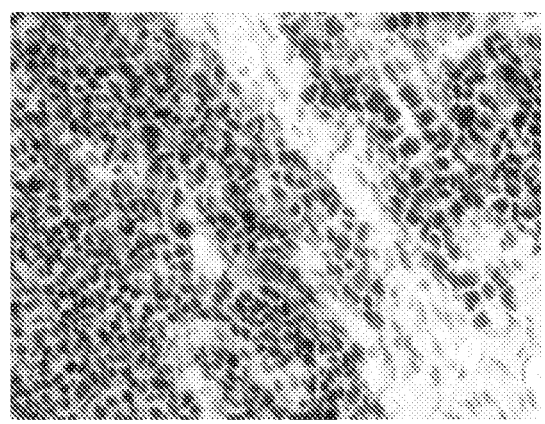
Figure 5A:
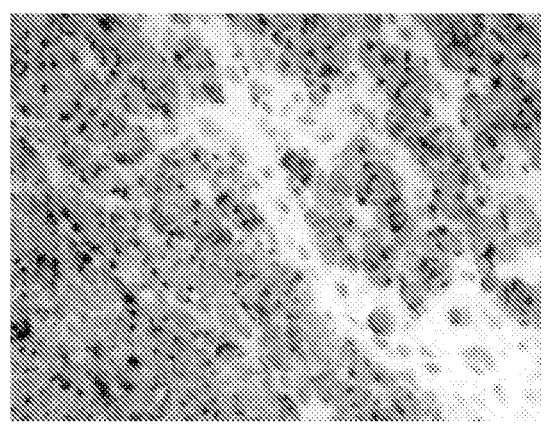
Figure 5B:
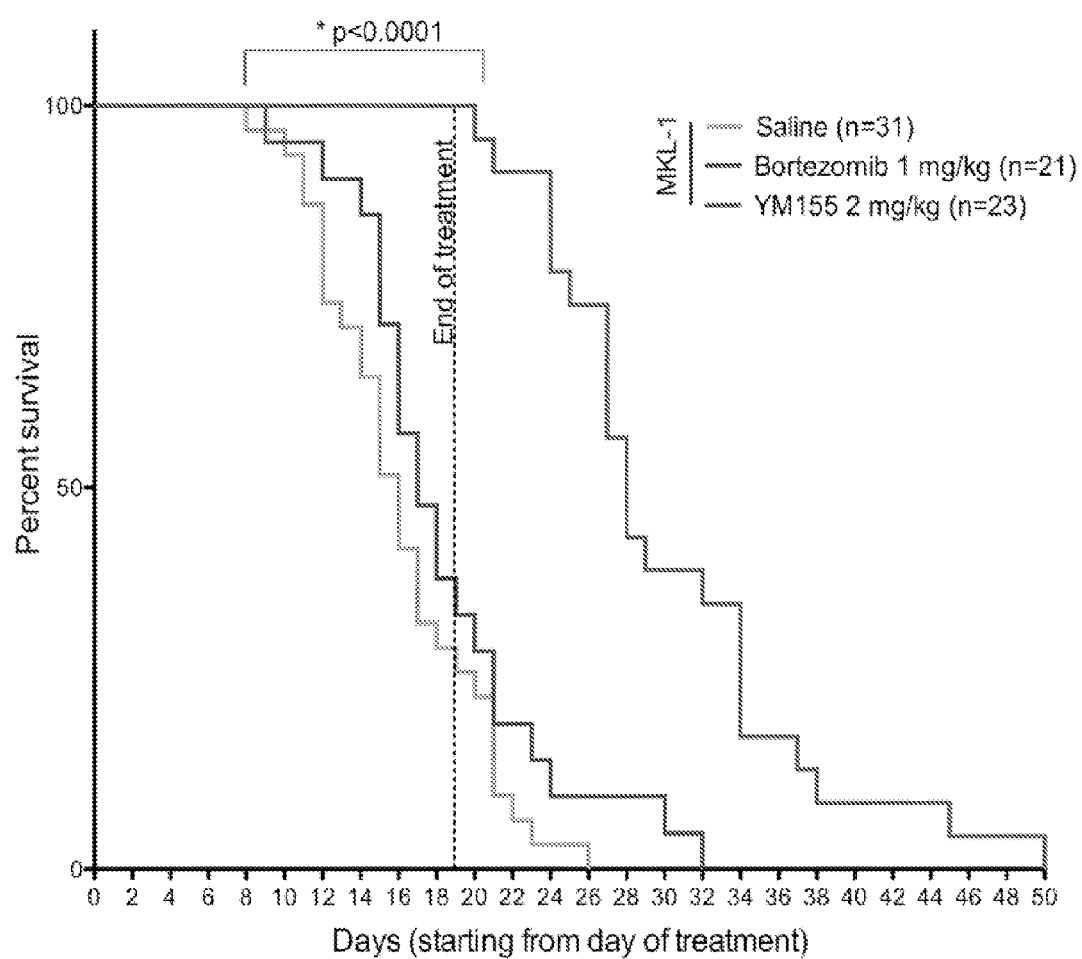
Figure 5C:
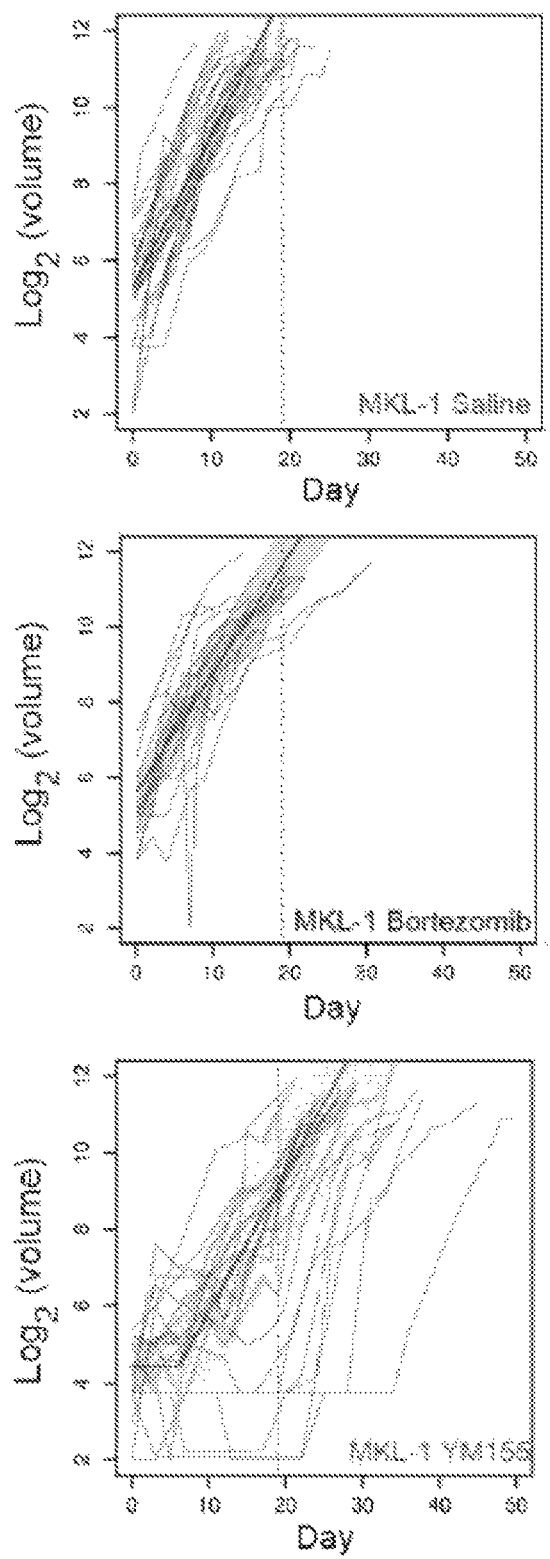

Two-tailed paired Student's t test was used to analyze statistical differences in qRT-PCR results. Mouse survival curves were estimated using the Kaplan-Meier product-limit method and were compared using the log-rank test (Graph-Pad Software, La Jolla, Calif.). A piecewise linear hierarchical Bayesian model (Zhao et al., Bayesian hierarchical changepoint methods in modeling the tumor growth profiles in xenograft experiments. *Clinical Cancer Res* 17, 1057 (Mar. 1, 2011)) was used to characterize differences in tumor volumes and growth between treatments. Examples of the Bayesian model are shown in FIG. 5C. A full description of the Bayesian methods used and data obtained therefrom may be found in provisional U.S. Patent Application No. 61/615, 546, incorporated herein by reference in its entirety.

Immunohistochemistry

Immunohistochemical staining of mouse tumor tissues was performed as previously described (Shuda et al., Human Merkel cell polyomavirus infection I. MCV T antigen expression in Merkel cell carcinoma, lymphoid tissues and lymphoid tumors. *Int J Cancer* 125, 1243 (Sep. 15, 2009)).

Results

Survivin Expression in MCV-Positive MCC

To identify pathways perturbed by MCV infection in MCC, we analyzed our DTS datasets to identify cellular genes differentially regulated between MCV-positive and MCV-negative MCC (Feng et al., Clonal integration of a polyomavirus in human Merkel cell carcinoma. *Science* 319, 1096 (Feb. 22, 2008)). We compared 400,000 cellular transcripts from MCV-positive and MCV-negative MCC tumors and found 1096 of 11,531 (9.5%) genes elevated >3 fold for the MCV-positive compared to the MCV-negative library.

We next identified sixty-four genes using Gene Ontology (GO) gene definitions (Ashburner et al., Gene ontology: tool for the unification of biology. The Gene Ontology Consortium. *Nature Genetics* 25, 25 (May, 2000)) directly involved in programmed cell death or cell cycle regulation (FIG. 1A). FIG. 1A shows that survivin oncoprotein mRNA expression is increased in MCV-positive MCC. FIG. 1A shows a DTS comparison of 64 genes involved in programmed cell death and cell cycle regulation, showing that survivin (BIRC5) mRNA transcripts (highlighted in bold) were seven-fold higher in a MCV-positive than an MCV-negative MCC DTS cDNA library. The relative expression of genes was normalized to total sequence reads for each MCC library. BIRC5a (Baculoviral inhibitor of apoptosis repeat-containing 5) mRNA encoding the survivin oncoprotein were increased 7 fold (p=2.90 e-10) for virus-positive compared to virus-negative MCC tumors (FIG. 1A). Other genes regulating programmed cell death, including TP53, cIAP2, XIAP, BAX, BCL2 and Caspase 3/6 transcripts, were not differentially expressed (FIG. 1A). Notably, some genes including TRAF2 and PI3K were significantly reduced in virus-positive compared to virus-negative MCC tumor libraries.

MCV Large T Induces Survivin Through Retinoblastoma Protein Targeting

Figure 1B:
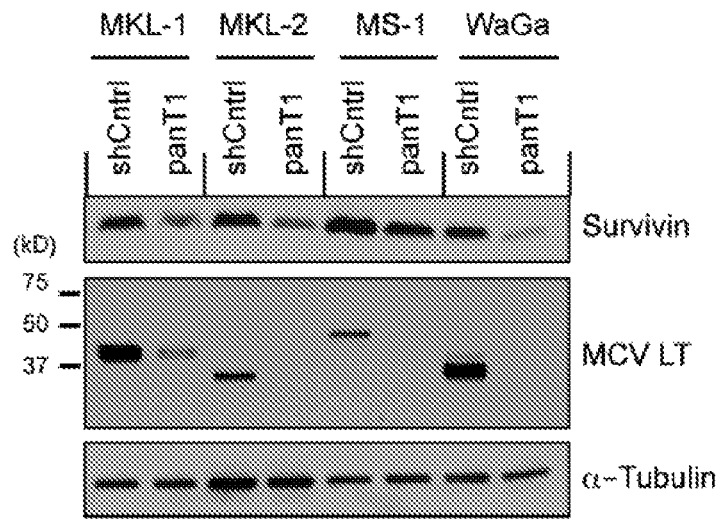
Figure 1B:
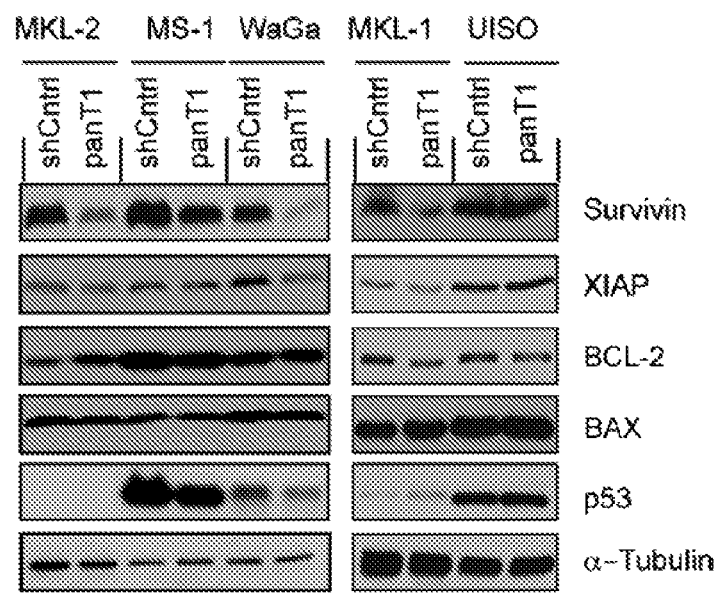
Figure 1C:
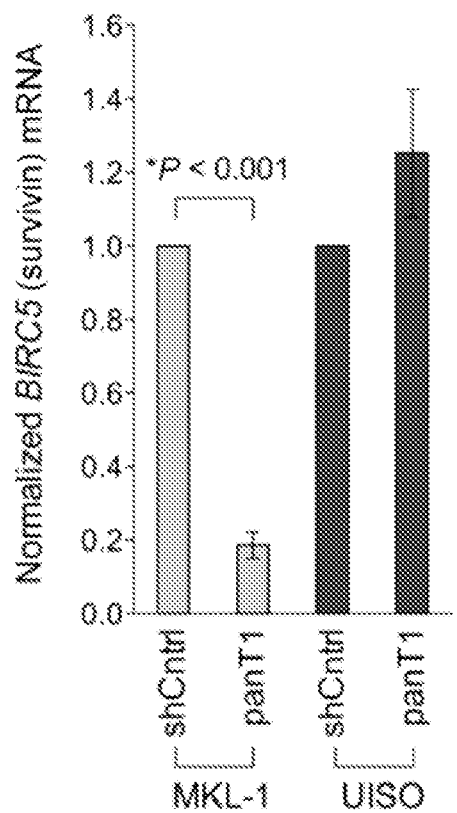

To determine if MCV T antigen increases survivin expression in MCC, we used an RNAi lentivirus (panT1shRNA) targeting MCV T antigen exon1 that selectively knocks down all MCV T antigen isoforms in MCC cells (Houben et al., Merkel cell polyomavirus-infected Merkel cell carcinoma cells require expression of viral T antigens. *J Virol* 84, 7064 (July, 2010)). MCV-positive MCC cells infected with this lentivirus undergo non-apoptotic cell death when MCV oncoprotein expression is inhibited (Houben et al., Merkel cell polyomavirus-infected Merkel cell carcinoma cells require expression of viral T antigens. *J Virol* 84, 7064 (July, 2010)). MCV T antigen reduction correlated with survivin reduction in all MCV-positive MCC cell lines, but not in any of the MCV-negative cell lines, in these knockdown experiments (FIG. 1B). FIG. 1B shows that MCV T antigen increases survivin expression. Lentiviral MCV T antigen exon1 knockdown (panT1) decreased survivin protein expression among four MCV-positive MCC cell lines (left panel). shCntrl is a scrambled shRNA control lentivirus. No consistent changes in XIAP, BCL-2, Bax or p53 protein levels are seen after MCV T antigen knockdown among MCC cell lines (FIG. 1B, right panel). MKL-1, MKL-2, MS-1 and WaGa are MCV positive and UISO is MCV negative. The degree of survivin decrease with T antigen knockdown ranged from modest in MS-1 to near-complete in WaGa cell lines (FIG. 1B). This effect is at the level of transcription rather than translation since BIRC5a mRNA is significantly reduced by T antigen knock down (FIG. 1C). FIG. 1C shows MCV T antigen increases survivin transcription. Survivin mRNA levels were reduced in MKL-1 but not UISO cells after T antigen knockdown indicating that T antigen acts survivin transcription. Survivin mRNA was measured by qRT-PCR and normalized to β-actin mRNA. The experiments were performed in triplicate and repeated two times (mean±SEM).

Figure 1D:
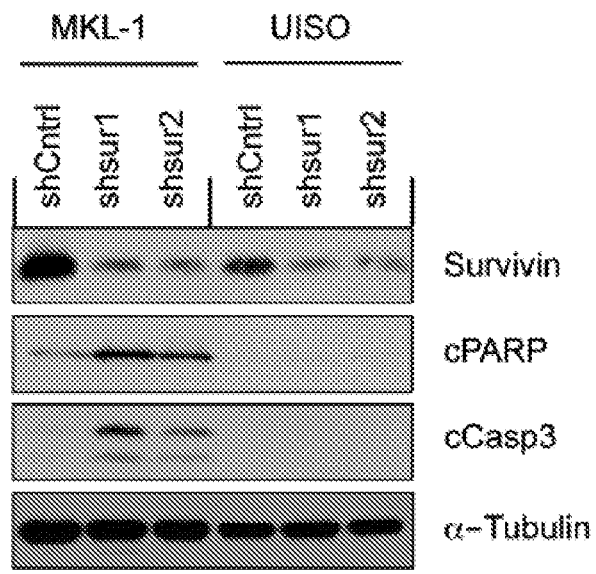

Use of an shRNA that selectively targets only the small T antigen isoform (Shuda et al., Human Merkel cell polyomavirus small T antigen is an oncoprotein targeting the 4E-BP1 translation regulator. *J Clin Invest*, (Aug. 15, 2011)), however, did not affect survivin expression (FIG. 6), suggesting increased survivin transcription may be dependent on MCV LT but not small T antigen (LT alone knockdown is not achievable due to the overlapping structure of the T antigen cistron). In contrast to survivin, no consistent changes in protein expression for p53, XIAP, Bcl-xL, Mcl-1, Bad, Bik, Bmf, Bim, Puma, Bcl-2 or Bax proteins (FIG. 1B and Houben et al., Merkel cell polyomavirus-infected Merkel cell carcinoma cells require expression of viral T antigens. *J Virol* 84, 7064 (July, 2010)), or for cleaved polyADP ribose polyomerase (PARP), cleaved caspase 3, cleaved caspase 6 or cleaved caspase 9 proteins (FIG. 7), was seen after panT1 knock down in MCV-positive cells. These results are consistent with our DTS findings suggesting that MCV T antigen selectively activates BIRC5a transcription. We next sought to determine the importance of survivin expression to survival of MCV-positive and MCV-negative MCC cells. Only partial suppression of survivin expression was achieved by shRNA BIRC5a targeting, which still generated marked apoptotic cell death of MCV-positive MKL-1 cells but not MCV-negative UISO cells (FIG. 1D). FIG. 1D shows Survivin expression is required for MCV-positive MCC cell survival. Survivin was targeted for knock down with two shRNA lentiviral vectors, shsur1 and shsur2 in MKL-1 cells and UISO cells. MKL-1 cells initiate apoptosis after survivin knockdown, with increased expression of cleaved polyADP ribose polymerase (cPARP) and caspase 3 (cCasp3), whereas UISO cells are resistant to survivin knock down-induced apoptosis. Tubulin is used as a loading control.

To confirm that LT is the MCV T antigen isoform responsible for survivin activation, we cloned and expressed a tumor-derived LT (LT339) cDNA in nontransformed, primary BJ fibroblasts. Survivin protein levels increased three-fold with LT expression, compared to empty vector control (as measured by ECL and quantitative LICOR immunoblotting, FIGS. 2A and 2B). FIG. 2 shows MCV LT protein isoform induces survivin oncoprotein expression in human BJ cells by targeting retinoblastoma protein (RB). Also consistent with our knock down experiments (FIG. 1C), LT directly activates BIRC5a promoter transcription in BJ cells (FIG. 2C). FIG. 2 shows survivin mRNA levels increased in BJ cells expressing LT.339 protein but not in cells expressing the RB1 binding mutant LT.339LFCDK. BJ cells expressing either empty, LT.339 or LT.339LFCDK were serum starved for 48 hours and then harvested for RNA. Survivin mRNA was measured by qRT-PCR and normalized to β-actin mRNA. The experiments performed three times in triplicate (mean±SEM).

Figure 8:
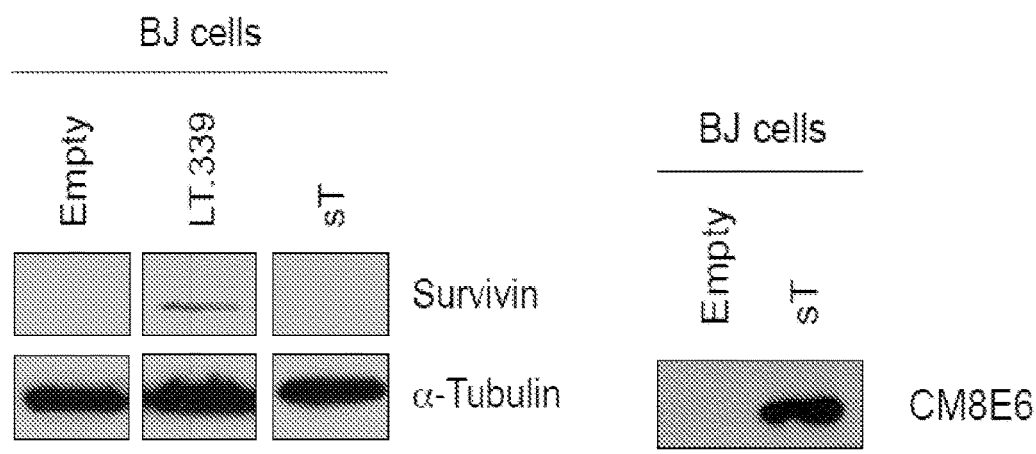
FIG. 8—MCV sT isoform does not induce survivin expression in BJ cells. BJ cells were transduced with either empty vector, tumor derived LT cDNA (LT.339) or small T antigen cDNA and immunoblotted for (Left) survivin and α-tubulin; (Right) CM8E6 (MCV T antigen exon 1). Lanes were run on the same gel, but were not contiguous.
Figure 9:
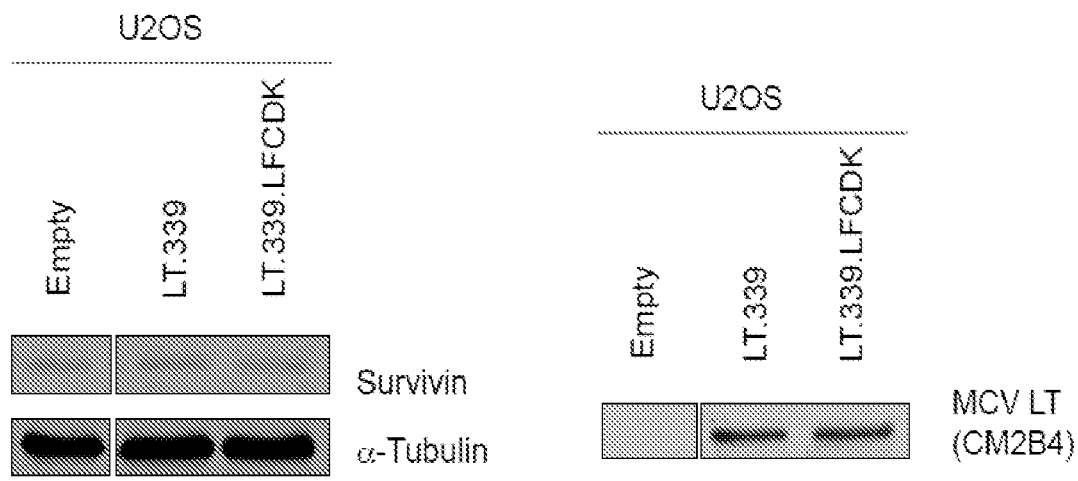
FIG. 9—MCV LT protein does not affect survivin oncoprotein expression in U2OS cells. U2OS cells were transduced and stably selected with empty vector, tumor derived LT cDNA (LT.339) or an LT cDNA with an inactive RB binding domain (LT.339.LFCDK) and immunoblotted for (Left) survivin and α-tubulin (LICOR); (Right) MCV Large T antigen (using CM2B4 antibody). Lanes were run on the same gel, but were not contiguous.

This is mediated by a specific domain (LXCXE) in LT responsible for sequestration of RB1. Both cyclin E and E2F1, required for cell cycle entry (Ohtani et al., Regulation of the cyclin E gene by transcription factor E2F1. *Proceedings of the National Academy of Sciences of the United States of America* 92, 12146 (Dec. 19, 1995)), are repressed by active RB1 and were used as markers for RB-regulated gene expression. MCV LT339 activates expression of these proteins in BJ cells, whereas a point mutation in LT339 (changing LFCDE to LFCDK) that prevents RB1 binding (Shuda et al., T antigen mutations are a human tumor-specific signature for Merkel cell polyomavirus. *Proc Natl Acad Sci USA* 105, 16272 (Oct. 21, 2008)), abolishes induction of cyclin E, E2F1 and survivin (FIG. 2A). FIG. 2A shows BJ cells were transduced with either empty vector, a tumor-derived LT cDNA (LT.339) or an LT cDNA with an inactive RB binding domain (LT.339LFCDK). Immunoblotting reveals that MCV LT.339 induces survivin expression but LT.339LFCDK does not. A similar pattern is seen for other S phase cell cycle proteins such E2F1 and cyclin E that are also transcriptionally repressed by RB. MCV small T expressed alone in BJ cells did not increase survivin oncoprotein expression (FIG. 8) In contrast to primary BJ fibroblasts, we did not find that MCV LT markedly increased survivin expression in cell lines that had been already transformed, including 293HEK and U2OS cells (FIG. 9).

Survivin as a Target for MCC Chemotherapy

Figure 3A:
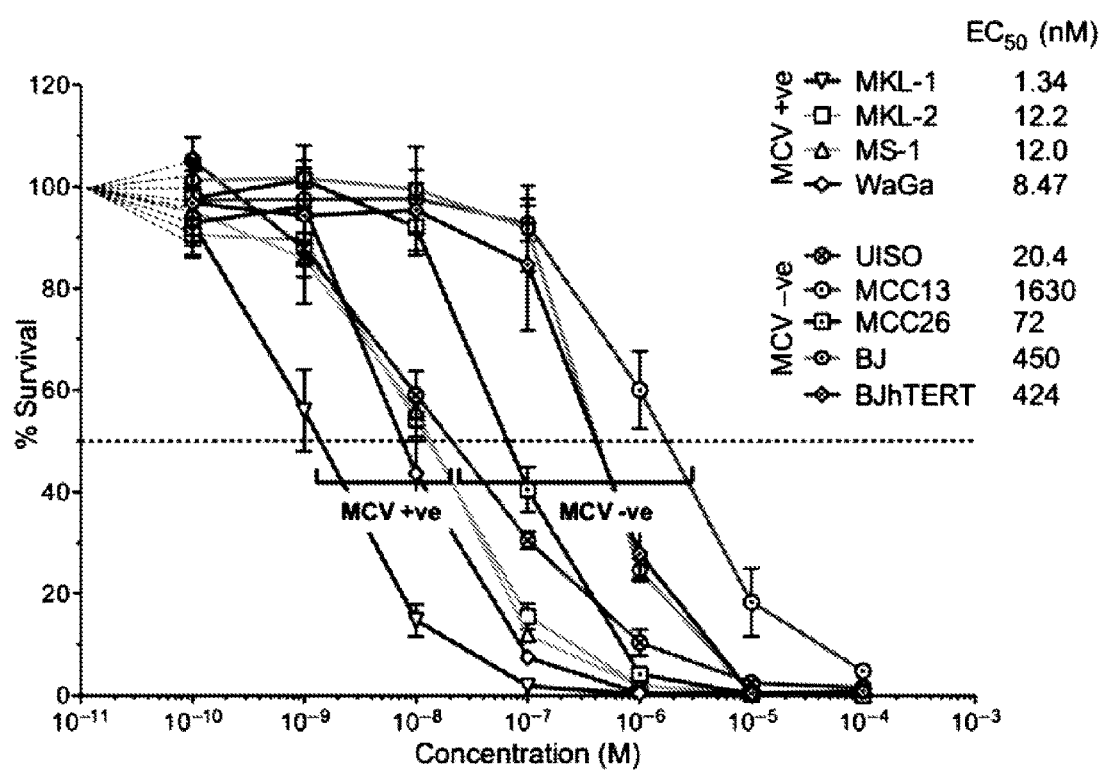
FIG. 3—The survivin promoter inhibitor YM155 also inhibits MCC cell line: (A) Dose-dependent growth curves at 48 h for YM155-treated cell lines. MCV-negative MCC13, BJ and BJhTERT cells showed relative resistance to YM155 treatment, whereas all MCV-positive cell lines (MKL-1, MKL-2, MS-1 and WaGa) were sensitive to YM155. MCV-negative UISO and MCC26 had intermediate sensitivity to the YM155; (B) Trypan blue vital dye exclusion assay showed dose-dependent cell killing at 48 h for MKL-1 cells whereas UISO cells are relatively less sensitive and BJ cells are resistant to YM155; (C) Dose-dependent decrease in MKL-1 cell survivin protein expression after 12 h YM155 treatment.

Given the apparent importance of MCV-induced survivin expression to MCC cell survival, we examined YM155, is an imidazolium small molecule inhibitor of the survivin promoter that is currently undergoing Phase II trials for prostate cancer (Nakahara et al., YM155, a novel small-molecule survivin suppressant, induces regression of established human hormone-refractory prostate tumor xenografts. *Cancer Res* 67, 8014 (Sep. 1, 2007); A. Tolcher et al., A phase II study of YM155, a novel small-molecule suppressor of survivin, in castration-resistant taxane-pretreated prostate cancer. *Annals of Oncology* (Aug. 22, 2011); Iwasa et al., Marked anti-tumour activity of the combination of YM155, a novel survivin suppressant, and platinum-based drugs. *Br J Cancer* 103, 36 (Jun. 29, 2010)). YM155 is both highly active and selective for inhibiting MCV-positive MCC cell growth in vitro as measured by Cell-Titer Glo assays ($EC_{50}$ 1.34 nM to 12.2 nM) (FIG. 3A). FIG. 3 shows the survivin promoter inhibitor YM155 also inhibits MCC cell line. FIG. 3A shows dose-dependent growth curves at 48 h for YM155-treated cell lines. MCV-negative MCC13, BJ and BJhTERT cells showed relative resistance to YM155 treatment, whereas all MCV-positive cell lines (MKL-1, MKL-2, MS-1 and WaGa) were sensitive to YM155. MCV-negative UISO and MCC26 had intermediate sensitivity to the YM155.

Figure 3B:
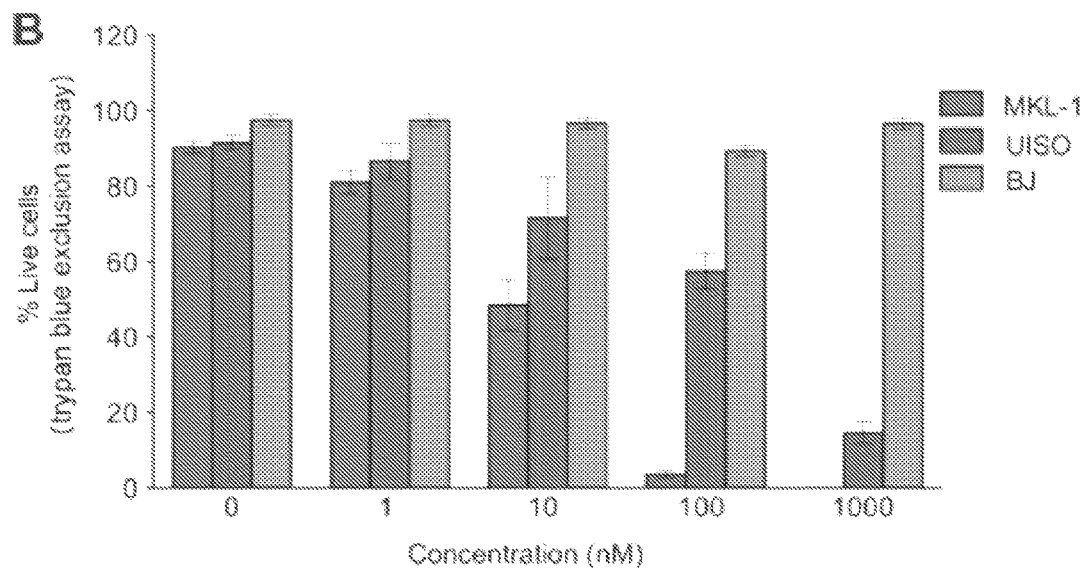
Figure 3C:
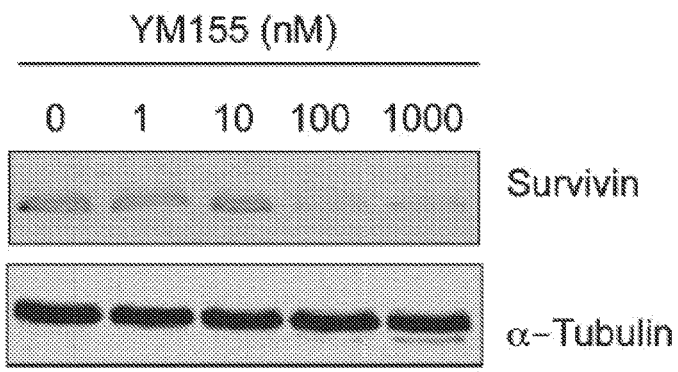

MCV-negative MCC cell line growth is also inhibited by YM155 but this occurs at concentrations 1-2 orders of magnitude higher than for MCV-positive MCC cells. YM155 treatment for 48 hours at 10-100 nM preferentially killed MKL-1 compared to UISO cells as measured by trypan blue staining (FIG. 3B) and by lactate dehydrogenase release assays (not shown). FIG. 3B shows trypan blue vital dye exclusion assay showed dose-dependent cell killing at 48 h for MKL-1 cells whereas UISO cells are relatively less sensitive and BJ cells are resistant to YM155. Survivin protein was reduced in MKL-1 cells after YM155 treatment, consistent with YM155's proposed mechanism of action in inhibiting the BIRC5a promoter (FIG. 3C). FIG. 3C shows dose-dependent decrease in MKL-1 cell survivin protein expression after 12 h YM155 treatment.

Figure 4A:
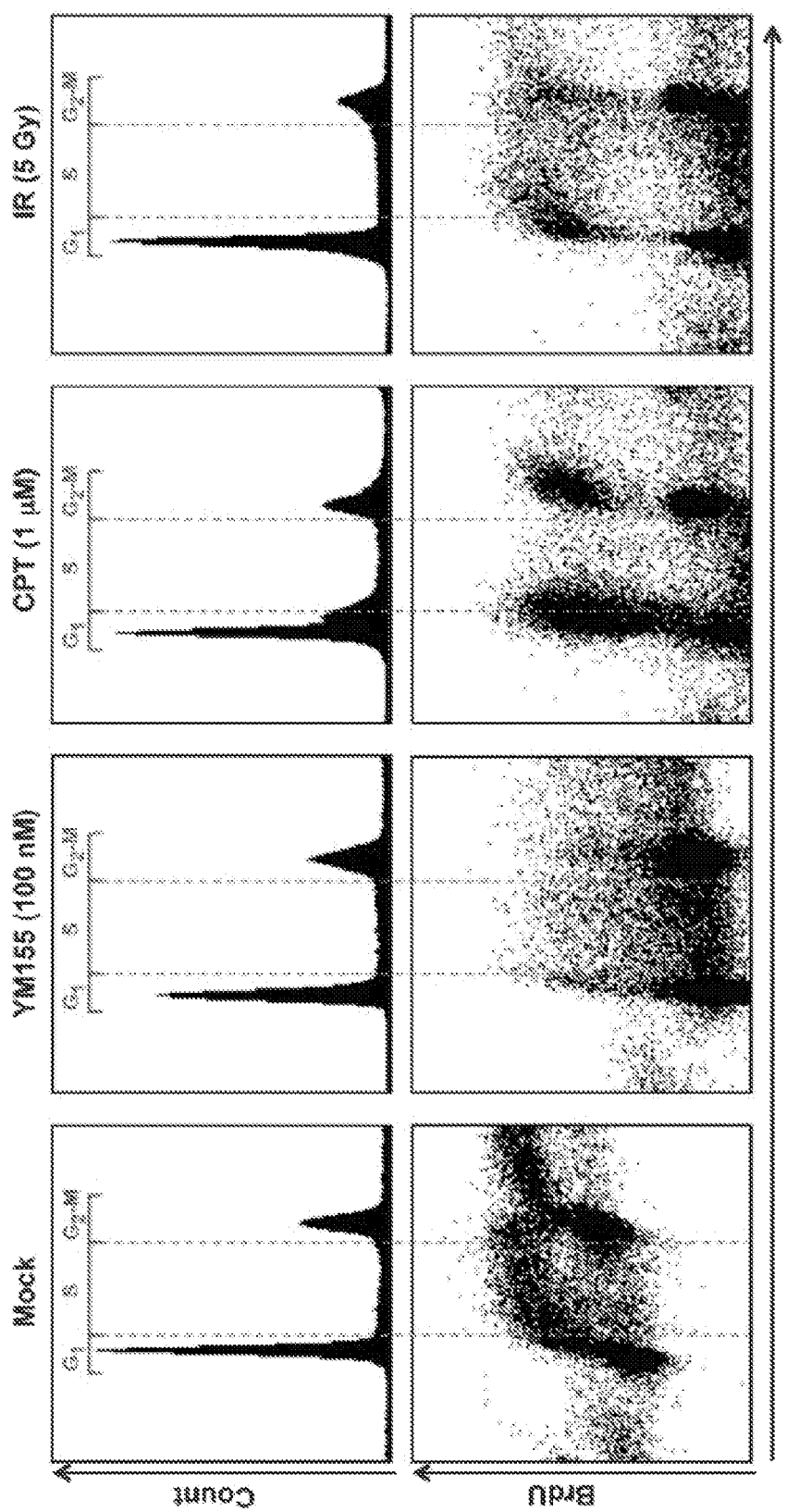
FIG. 4—Cell death phenotype of YM155 treated MCV positive MCC: (A) YM155 induces nonapoptotic cell death associated with autophagy in MKL-1 cells. MKL-1 cells were treated with DMSO, YM155 (100 nM) or bortezomib (100 nM) and immunoblotted for cPARP, cCaspase 3, LC3 and tubulin. In contrast to YM155, bortezomib, a proteasome inhibitor, activates MKL-1 cell apoptosis; (B) Cell cycle analysis reveals YM155 treated cells do not undergo mitotic catastrophe. MKL-1 cells were treated with DMSO, YM155 (100 nM) and camptothecin (CPT, 1 μM) for 12 h and then subjected to PI (upper panel) and BrdU staining (lower panel). Arrows show S phase BrdU incorporation without treatment, accumulation at G1 and G2 during CPT treatment, and near-complete loss of BrdU incorporation during YM155 treatment; (C) YM155 treatment initiates programmed cell death within 12-24 hours after treatment. MKL-1 cells were co-stained with CFDA (green, live) and PI (red, dead); (D) Column graphs represent mean and range quantitations (using ImageJ) of % CFDA positive and % PI positive cells.
Figures 4, 11A:
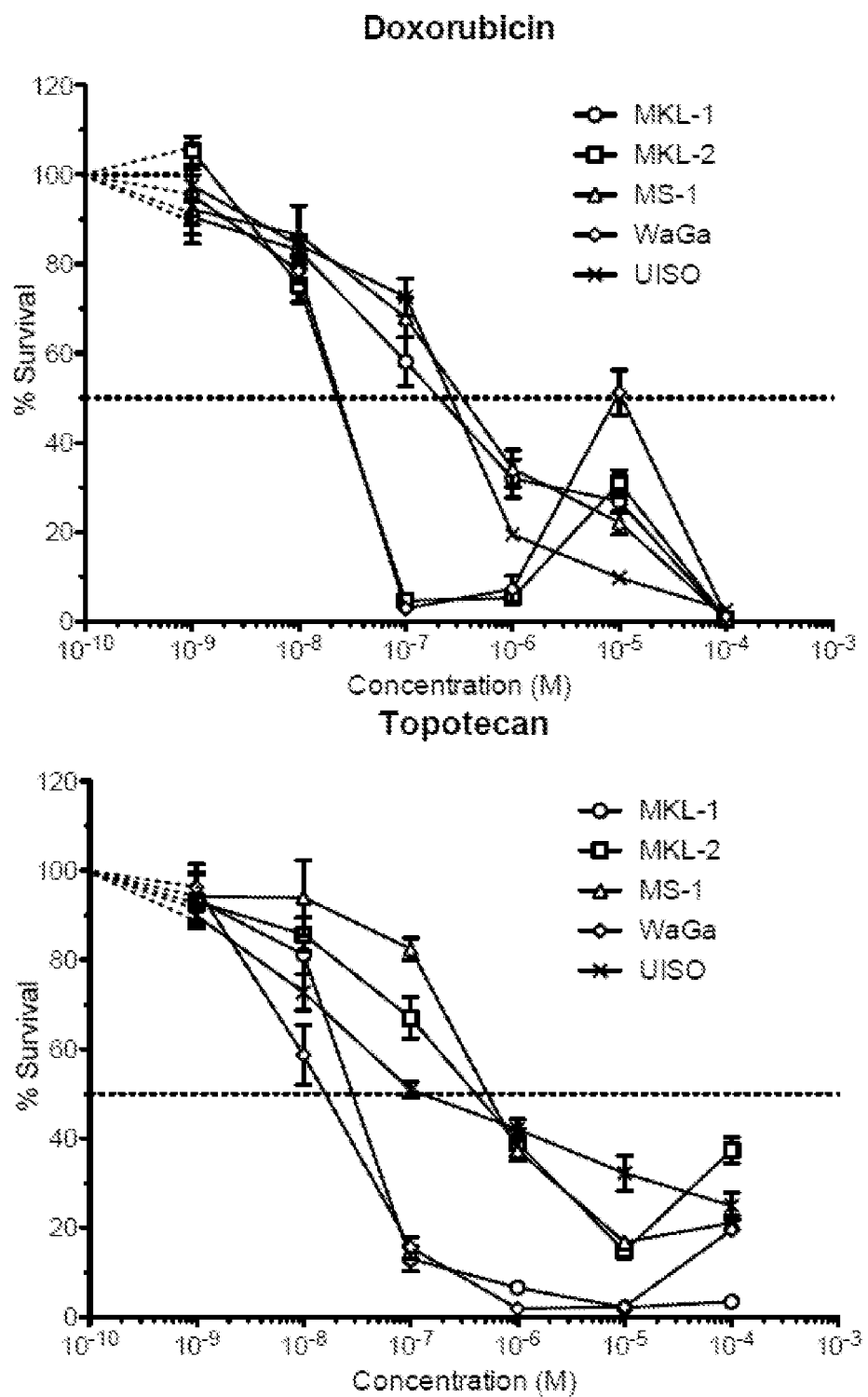

We next examined mechanisms of cell killing by YM155 in MCV-positive MCC cells. Survivin plays a role in mitotic progression and loss of survivin can lead to cell death through mitotic catastrophe (Tu et al., Suppression of survivin expression inhibits in vivo tumorigenicity and angiogenesis in gastric cancer. *Cancer Research* 63, 7724 (Nov. 15, 2003); Zhang et al., Survivin knockdown by short hairpin RNA abrogates the growth of human hepatocellular carcinoma xenografts in nude mice. *Cancer Gene Therapy* 17, 275 (April, 2010)). MCV-positive MCC, however, are slowly cycling cells (doubling time of 3 days, (Houben et al., Merkel cell polyomavirus-infected Merkel cell carcinoma cells require expression of viral T antigens. *J Virol* 84, 7064 (July, 2010)) and do not undergo G1 arrest or G2/M pileup as would occur with mitotic checkpoint activation in rapidly cycling cells (FIG. 4A, top panels). FIG. 4 shows cell death phenotype of YM155 treated MCV positive MCC. FIG. 4A shows cell cycle analysis reveals YM155 treated cells do not undergo mitotic catastrophe. MKL-1 cells were treated with DMSO, YM155 (100 nM) and camptothecin (CPT, 1 μM) for 12 h and then subjected to PI (upper panel) and BrdU staining (lower panel). Arrows show S phase BrdU incorporation without treatment, accumulation at G1 and G2 during CPT treatment, and near-complete loss of BrdU incorporation during YM155 treatment.

Instead, bromo-deoxyuridine (BrdU) incorporation into DNA reveals a profound inhibition of DNA synthesis at all phases of the cell cycle. FIG. 4A (arrow, bottom left panel) shows a normal inverted-U pattern for BrdU incorporation during S phase DNA synthesis in untreated MKL-1 cells. When the topoisomerase I inhibitor camptothecin is added (FIG. 4A, bottom right panel), accumulation of BrdU-positive cells in G1 and G2 occurs (arrows), consistent with activation of DNA damage response signaling in MKL-1. YM155 treatment, however, ablates BrdU incorporation in all phases of the cell cycle (FIG. 4A, center panel), most consistent with disruption of DNA replication forks and inhibition of new DNA synthesis.

Figure 4B:
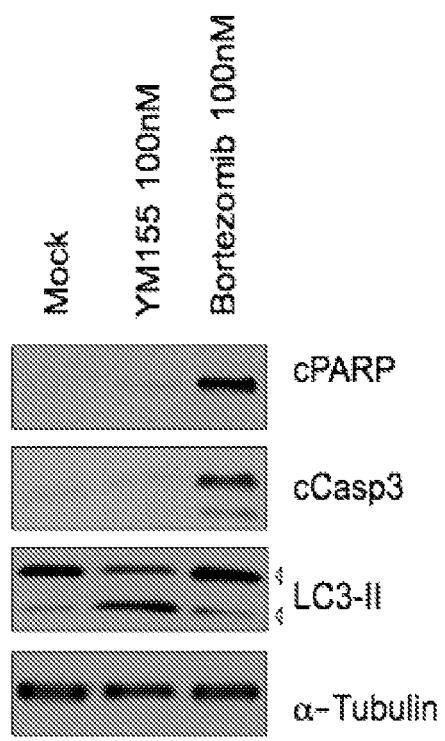
Figure 4D:
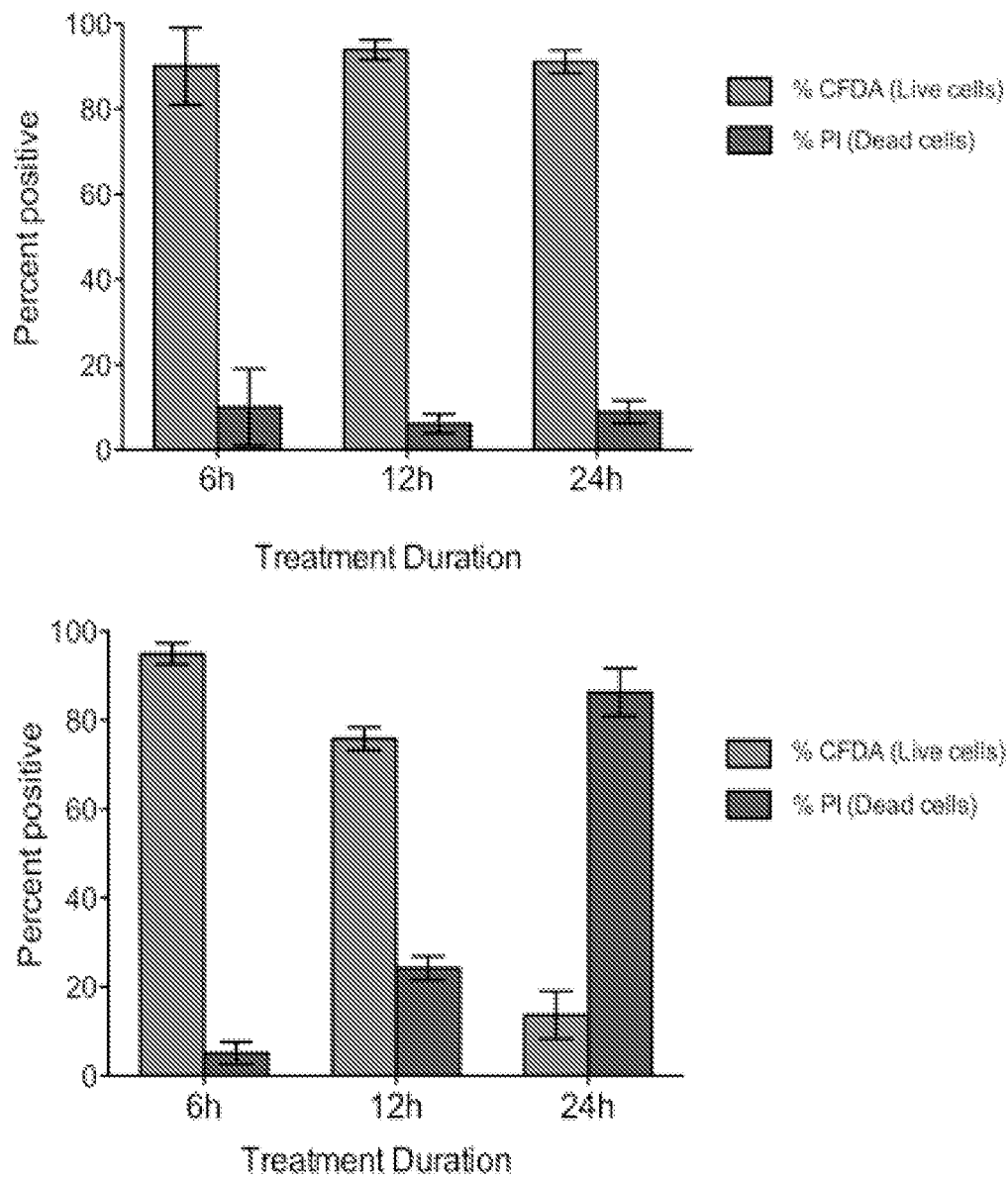
Figure 10A:
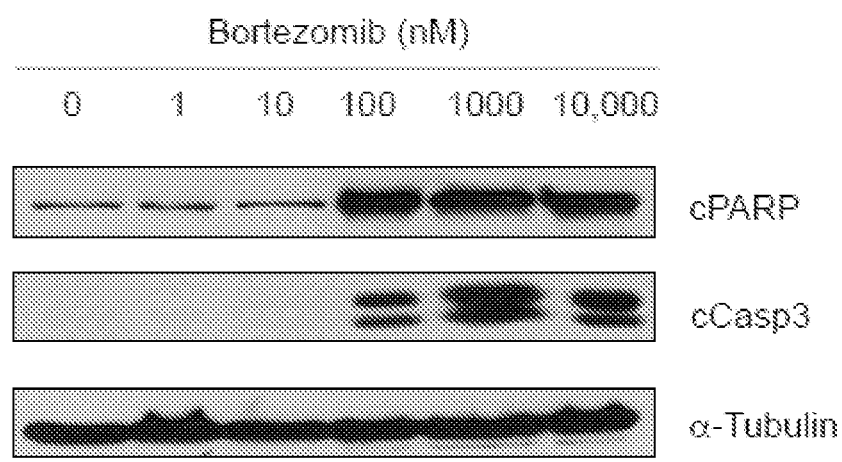
FIG. 10—Bortezomib induces apoptotic cell death in MCC cells: (A) MKL-1 cells were treated with bortezomib (1, 10, 100, 1000, and 10,000 nM) for 48 h; or (B) MKL-1 cells treated with 100 nM bortezomib for different time points; or (C) other MCC cell lines MKL-1, MKL-2, MS-1, WaGa and UISO) treated with 100 nM bortezomib for 48 h were tested for immunoblotting for cleaved caspase 3, cleaved PARP apoptotic markers and α-tubulin. 0.01% DMSO was used for mock-treatment control.
Figure 10B:
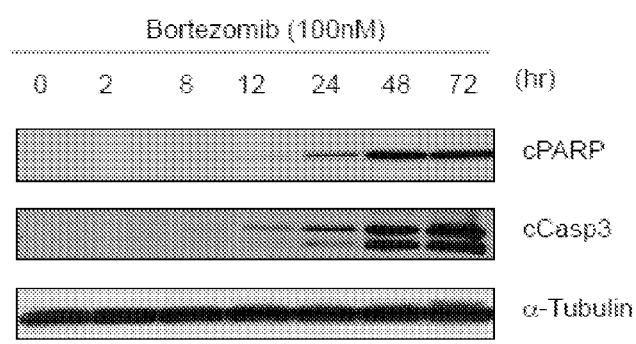
Figure 10C:
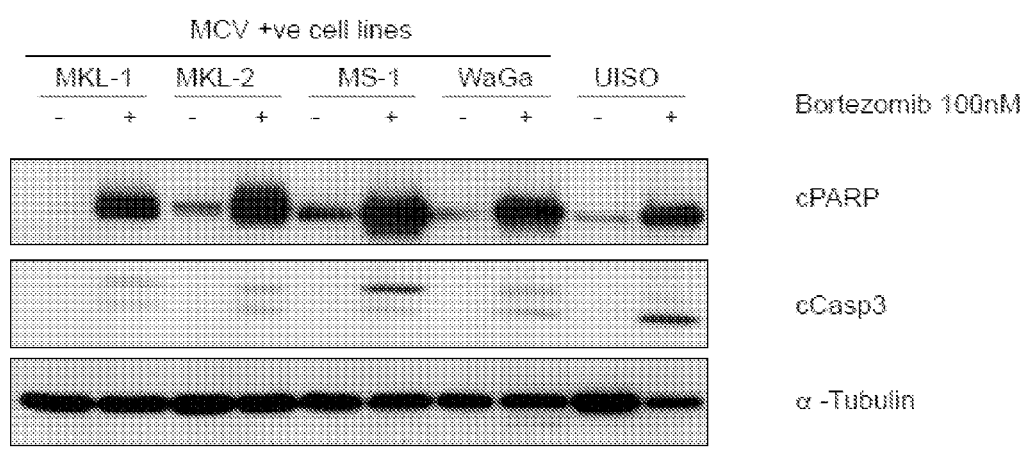

YM155 treatment results in early commitment to non-apoptotic programmed cell death. No evidence of apoptosis was present, measured by caspase 3 and PARP cleavage (FIG. 4B) when MKL-1 cells were treated with 100 nM YM155 for 48 hours, but YM155 did not initiate LC3-II accumulation, a marker for cell autophagy. FIG. 4B shows YM155 induces nonapoptotic cell death associated with autophagy in MKL-1 cells. MKL-1 cells were treated with DMSO, YM155 (100 nM) or bortezomib (100 nM) and immunoblotted for cPARP, cCaspase 3, LC3 and tubulin. In contrast to YM155, bortezomib, a proteasome inhibitor, activates MKL-1 cell apoptosis This is not sue to loss of apoptosis pathway signaling since treatment with the proteasome inhibitor bortezomib (Velcade) activated PARP and caspase cleavage (FIG. 4B; FIG. 10). Commitment to YM155 cell death occurs relatively quickly and irreversibly: when MKL-1 cells were treated with 100 nM YM155 for 3, 6 or 12 hours, followed by wash out with complete cell culture medium, only 51%, 3% and 1.8% of cells, respectively, remained viable at 48 hours as measured by trypan blue dye exclusion. This was confirmed by a cell viability assay using propidium iodide (PI, dead) and carboxyfluorescein diacetate (CFDA, alive) co-staining (FIG. 4C). FIG. 4C shows YM155 treatment initiates programmed cell death within 12-24 hours after treatment. MKL-1 cells were co-stained with CFDA (green, live) and PI (red, dead). In FIG. 4D, column graphs represent mean and range quantitations (using ImageJ) of % CFDA positive and % PI positive cells. Twelve to 24 hours of 100 nM YM155 treatment causes MKL-1 cells to lose membrane integrity, becoming positive for PI and negative for CFDA staining.

Figures 1, 11B:
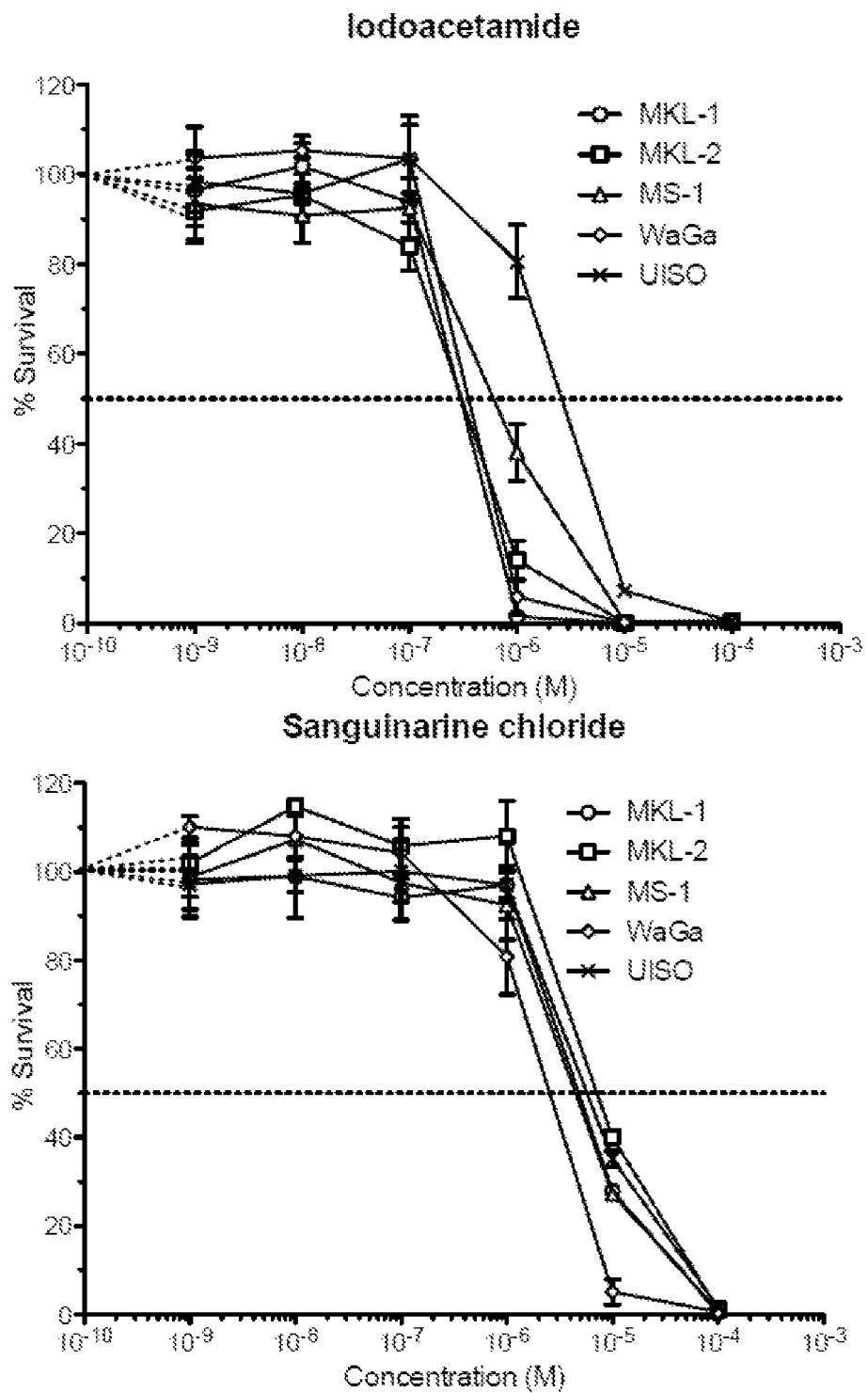
Figures 2, 11B:
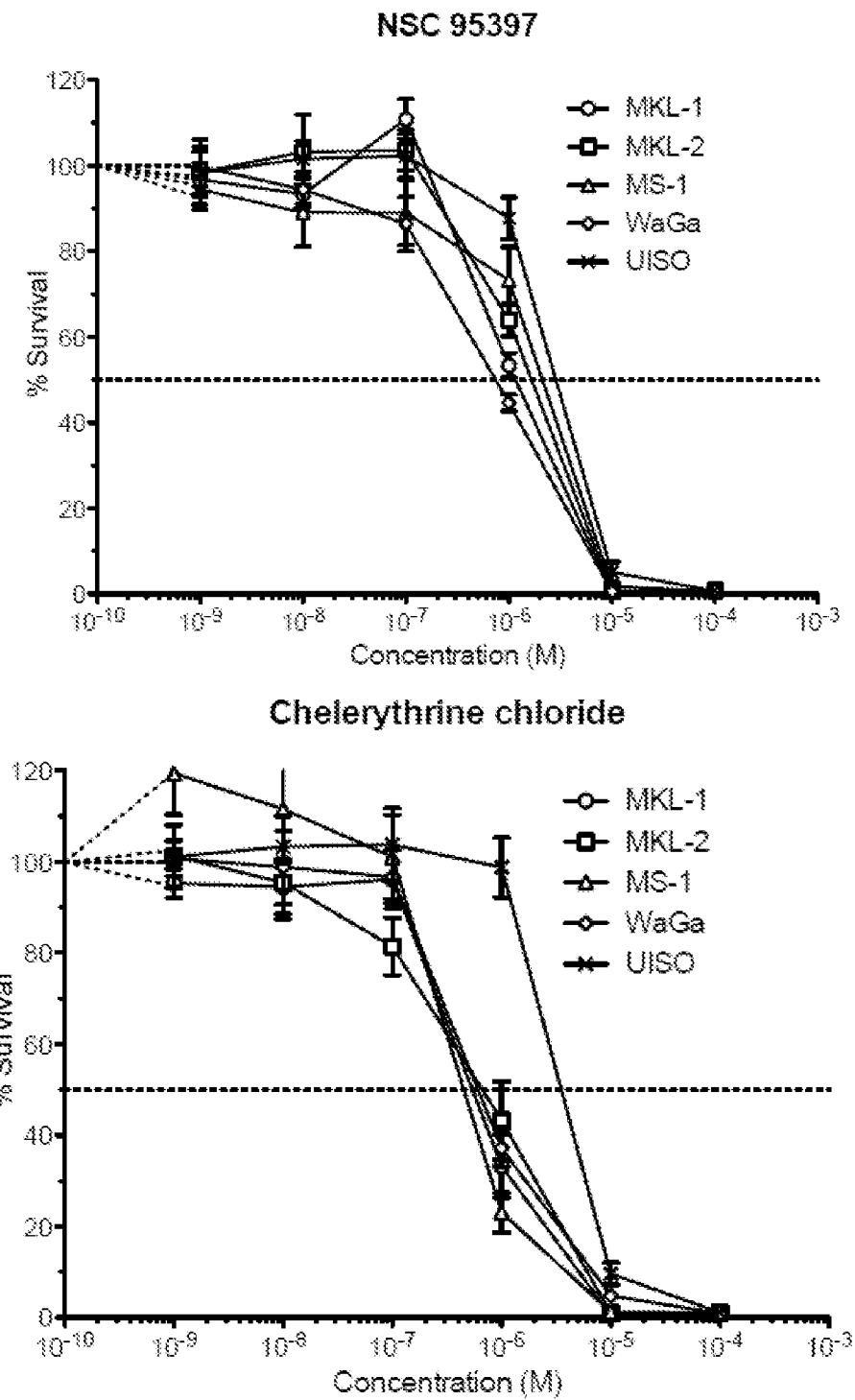
Figures 3, 11B:
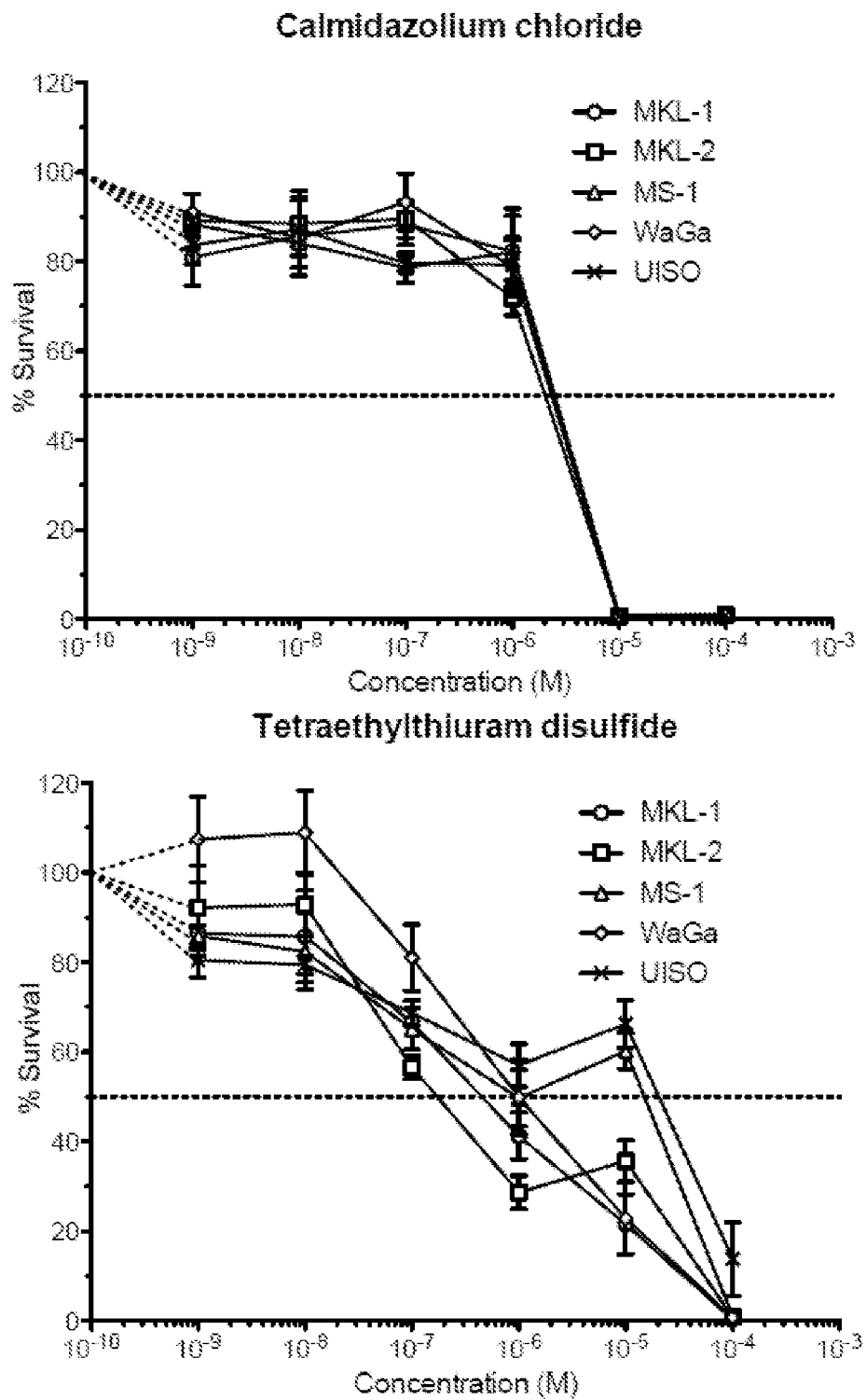
Figures 4, 11B:
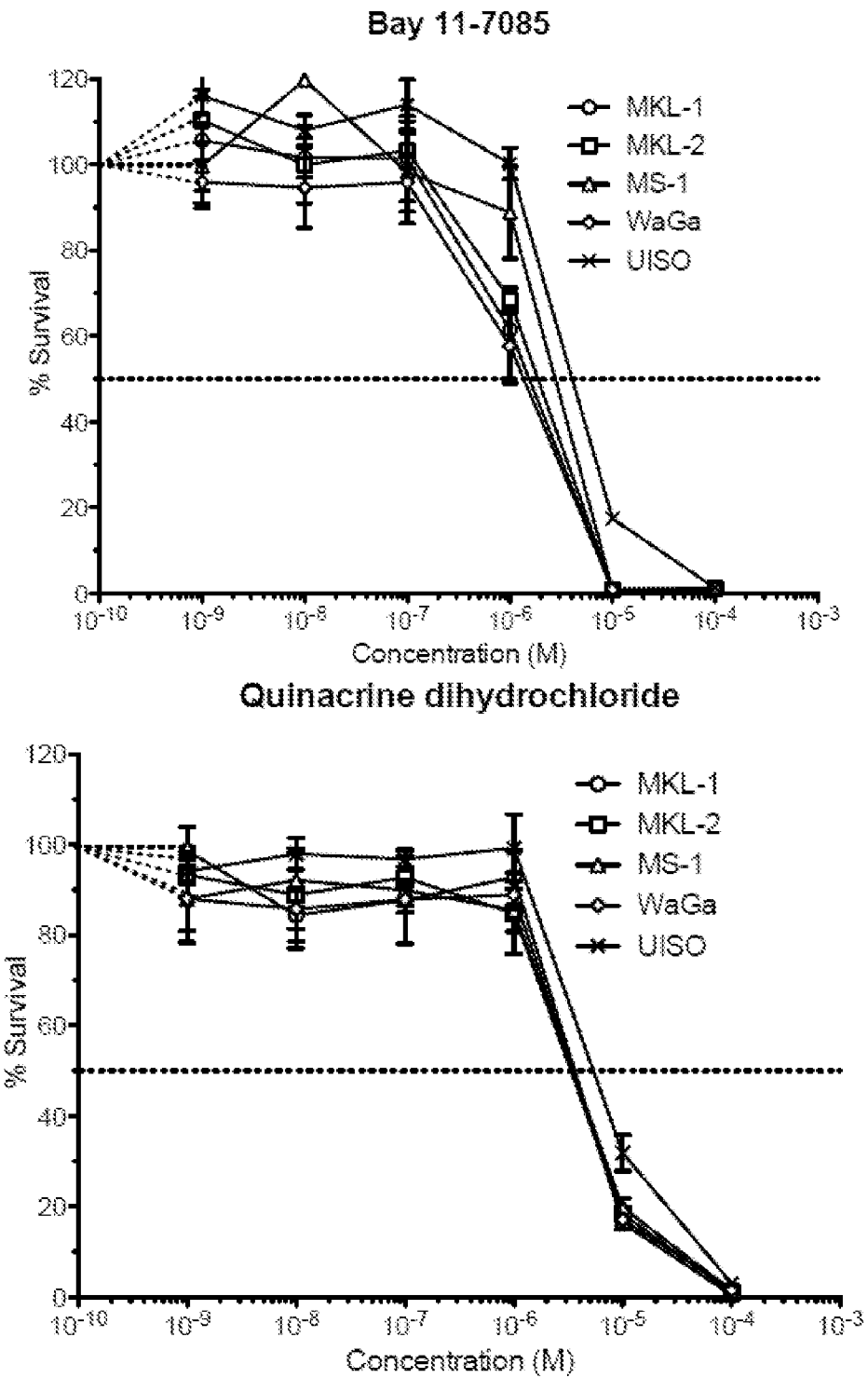

To search for other MCC chemotherapeutics, we performed a two-stage cytotoxicity library screen on 1,360 pharmacologically-active drug compounds (see FIGS. 11A and 11B, see also priority application, U.S. Provisional Patent Application No. 61/615,546, filed Mar. 26, 2012, which is incorporated herein by reference in its entirety), including 1,280 drugs from the Library of Pharmacologically Active Compounds (LOPAC) (Sigma Aldrich), 89 drugs from the National Cancer Institute's Approved oncology drug set II (19 compounds in common with LOPAC1280), 6 compounds targeting SV40 LT ATPase activity (Wright et al., Inhibition of Simian Virus 40 replication by targeting the molecular chaperone function and ATPase activity of T antigen. *Virus Res* 141, 71 (April, 2009); Seguin et al., High-Throughput Screening Identifies a Bisphenol Inhibitor of SV40 Large T Antigen ATPase Activity. *Journal of Biomolecular Screening*, (Sep. 23, 2011)) and 4 compounds targeting MDM2 to activate p53 (Czarna et al., Robust generation of lead compounds for protein-protein interactions by computational and MCR chemistry: p53/Hdm2 antagonists. *Angewandte Chemie* 49, 5352 (Jul. 19, 2010); Popowicz et al., Structures of low molecular weight inhibitors bound to MDMX and MDM2 reveal new approaches for p53-MDMX/MDM2 antagonist drug discovery. *Cell Cycle* 9, 1104 (Mar. 15, 2010)). These compounds were screened at $10^{-5}$ M for >90% inhibition of MKL-1 cell growth in a Cell-Titer Glo assay (Promega). Notably, mTOR inhibitors (Torin1, PP242, everolimus and rapamycin), antiviral compounds (ribavirin, acyclovir) and MDM-2 inhibitors, reported to be active in other viral cancers (e.g., nutlin-3 (Sarek et al., Reactivation of the p53 pathway as a treatment modality for KSHV-induced lymphomas. *J Clin Invest* 117, 1019 (April, 2007); Petre et al., Functional p53 Signaling in Kaposi's Sarcoma-Associated Herpesvirus Lymphomas. Implications for Therapy. *J Virol* 81, 1912 (February, 2007))—were not active in our screen. This is consistent with previous findings on loss of MCV replication activity (Shuda et al., T antigen mutations are a human tumor-specific signature for Merkel cell polyomavirus. *Proc Natl Acad Sci USA* 105, 16272 (Oct. 21, 2008)) and MCV sT targeting of cap-dependent translation downstream of mTOR (Shuda et al., Human Merkel cell polyomavirus small T antigen is an oncoprotein targeting the 4E-BP 1 translation regulator. *Journal Clin Invest*, (Aug. 15, 2011)) in MCC tumor cells.

Figure 7:
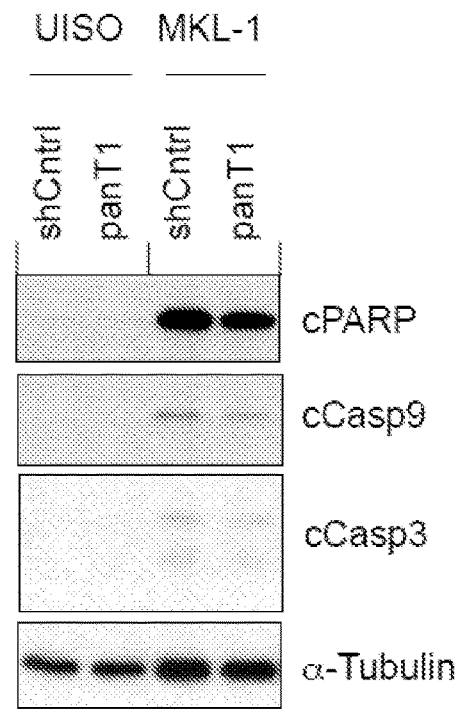
FIG. 7—T antigen knockdown does not affect caspase and PARP cleavage. UISO and MKL-1 cells with panT1 knockdown were tested for immunoblotting for cleaved caspase 3 and 9, cleaved PARP and α-tubulin.
Figure 11C:
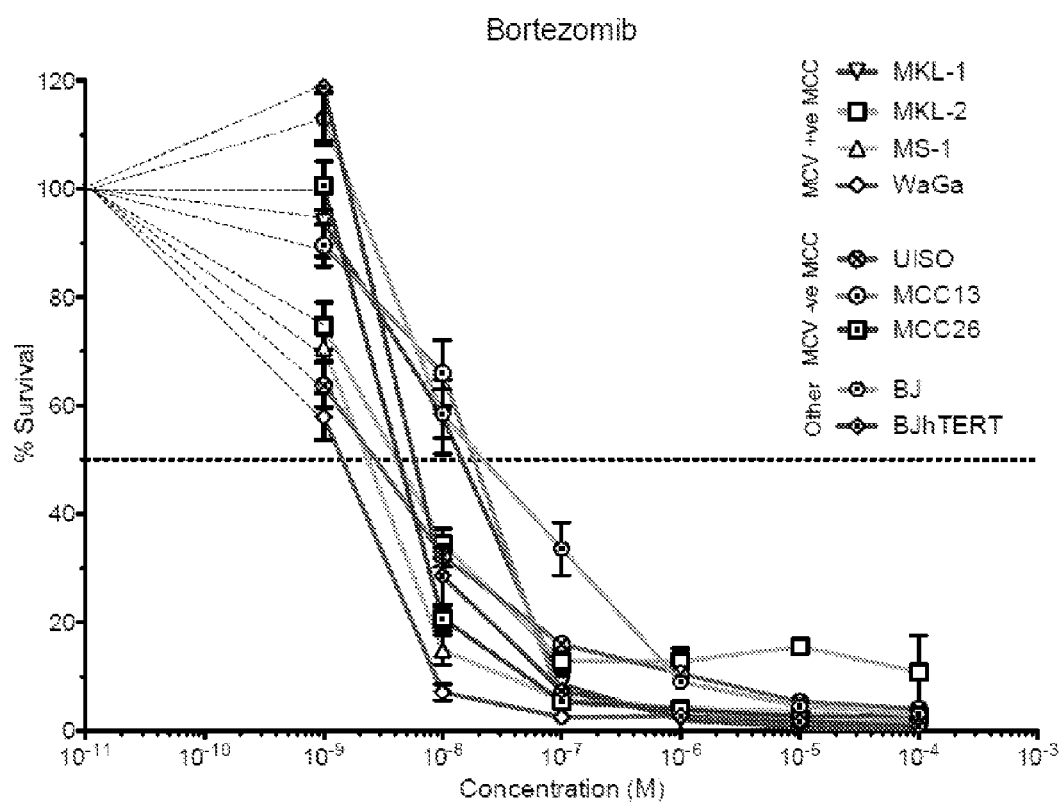
FIG. 11—Dose response curves for drug screen candidates. MCC cell lines and other human cancer cell lines were treated with compounds identified from the screen at increasing doses. Cell viability was normalized to no drug conditions (% survival=100). Shown is the average and standard deviation for two independent experiments tested in triplicate: (A) topoisomerase inhibitors; (B) other drugs; (C) bortezomib; (D) bortezomib; and (E) YM155 tested on NCI-H69, 293, and U2OS cells.
Figure 11D:
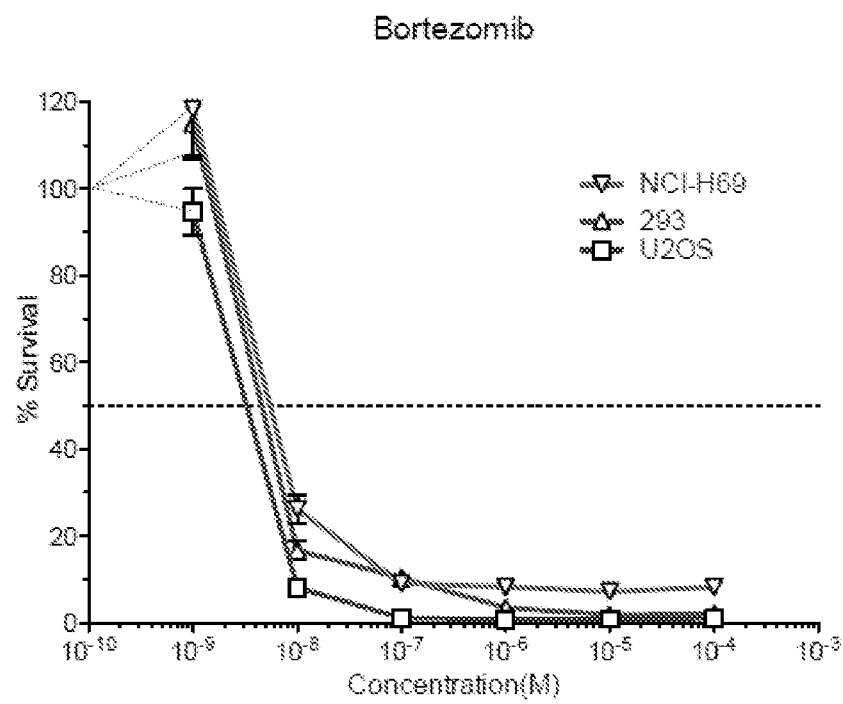
Figure 11E:
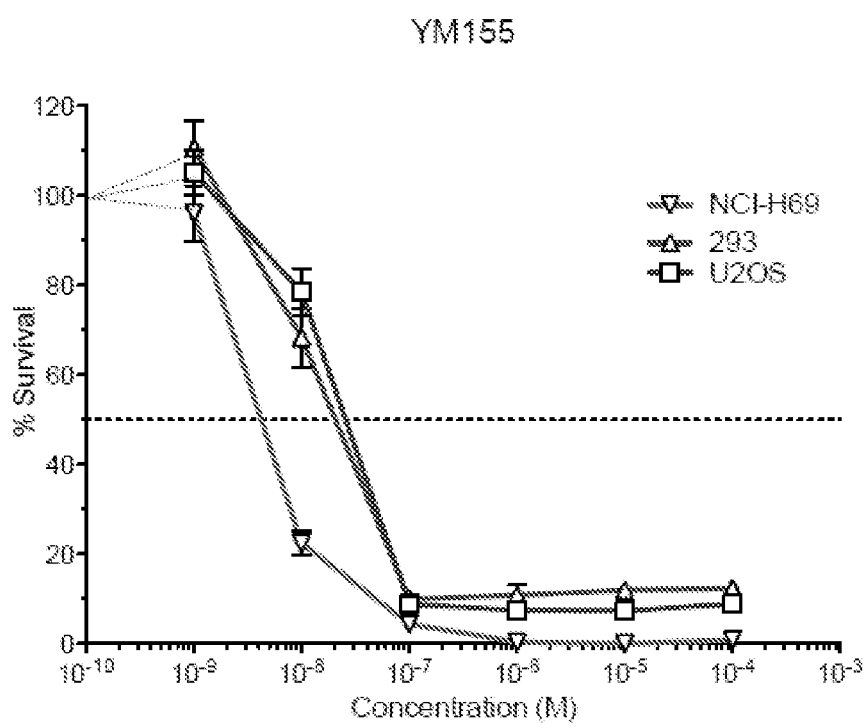

Eighteen (1.3%) drugs met our initial screening criterion for anti-MCC activity and were selected for secondary dose-dependent screening on MCV-positive and MCV-negative cell lines (Table 1). Only the proteasome-inhibitor bortezomib (Einsele, Bortezomib. *Recent Results Cancer Res* 184, 173 (2010)) was active in vitro at low doses ($EC_{50}$, 1.3-13.2 nM, FIG. 11C and FIG. 10). This activity, however, was not selective for MCV-positive cells (FIG. 7). Other agents, particularly topoisomerase I and II inhibitors, also inhibited MCC cell growth but were generally far less potent or had variable activity among different MCC cell lines (Table 1 and FIGS. 11A and 11B).

TABLE 1

EC$_{50}$ (µM) concentrations for MCC cell lines

| Drugs | MKL-1 | MKL-2 | MS-1 | WaGa | UISO |
|---|---|---|---|---|---|
| PROTEASOME INHIBITOR | | | | | |
| Bortezomib | 0.013 | 0.005 | 0.002 | 0.001 | 0.003 |
| TOPOISOMERASE INHIBITORS | | | | | |
| Ellipticine | 3.2 | 6.5 | 6.9 | 3.0 | 1.1 |
| Amsacrine hydrochloride | 0.11 | 3.0 | 7.5 | 0.25 | 2.6 |
| Teniposide | 0.010 | 2.8 | 3.0 | 0.026 | 7.3 |
| Valrubicin | 0.23 | 2.8 | 9.9 | 0.32 | 4.0 |
| Mitoxantrone | 0.006 | 1.3 | 1.6 | 0.014 | 0.97 |
| Daunorubicin | 0.015 | 0.086 | 0.15 | 0.018 | 1.4 |
| Doxorubicin | 0.21 | 0.022 | 0.37 | 0.022 | 0.25 |
| Topotecan | 0.028 | 0.43 | 0.62 | 0.015 | 0.17 |
| OTHERS | | | | | |
| Iodoacetamide | 0.29 | 0.30 | 0.64 | 0.37 | 2.5 |
| Sanguinarine chloride | 5.3 | 8.4 | 4.9 | 2.5 | 6.5 |
| NSC 95397 | 1.2 | 1.5 | 1.8 | 0.73 | 2.8 |
| Chelerythrine chloride | 0.60 | 0.65 | 0.52 | 0.70 | 3.7 |
| Calmidazolium chloride | 2.2 | 1.7 | 2.1 | 2.1 | 2.0 |
| Tetraethylthiuram disulfide | 0.49 | 0.19 | 6.3 | 1.1 | 13 |
| Bay 11-7085 | 1.4 | 1.7 | 2.7 | 1.2 | 4.5 |
| Quinacrine dihydrochloride | 5.1 | 4.6 | 4.9 | 5.2 | 7.1 |

Effect of YM155 on Human MCC Xenografts in Mice

We developed an MKL-1 xenograft model to test the in vivo efficacy of YM155 and bortezomib on human MCC in NOD scid gamma (NSG) mice. Subcutaneous injection of MKL-1 cells generates tumors that are positive for MCV LT and CK20 (FIG. 5A) and progress to endpoint within 2-4 weeks after tumors are first detected. FIG. 5 shows YM155 inhibits growth of human MKL-1 MCC xenografts in NSG mice. FIG. 5A shows MKL-1 xenograft tumors stained with hematoxylin and eosin, MCV LT (CM2B4 antibody) and CK20 (magnification 40×). Mice were treated with bortezomib, YM155 or saline for three weeks once tumors became palpable. Bortezomib was administered at levels effective on multiple myeloma xenografts (LeBlanc et al., Proteasome inhibitor PS-341 inhibits human myeloma cell growth in vivo and prolongs survival in a murine model. *Cancer Res* 62, 4996 (Sep. 1, 2002)) (1 mg/kg, twice weekly subcutaneous injections). This did not significantly affect MCC tumor progression or volume compared to treatment with saline alone (p value=0.53, log-rank test). Bortezomib administration at this level was associated with mouse lethargy and weight loss, requiring temporary use of heat blankets and Hydrogel (ClearH$_2$O) to prevent animal loss during treatment.

Figures 5D, 6:
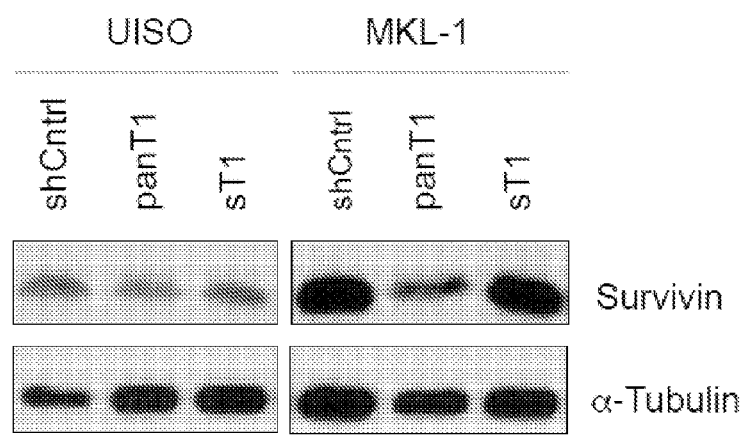
FIG. 6—MCV sT antigen knockdown does not affect survivin expression. UISO and ML-1 cells infected with sT1, which knockdown sT alone as well as panT1 shRNA lentiviruses were tested for immunoblotting for survivin and α-tubulin. Lanes were run on the same gel, but were not contiguous.
Figure 12:
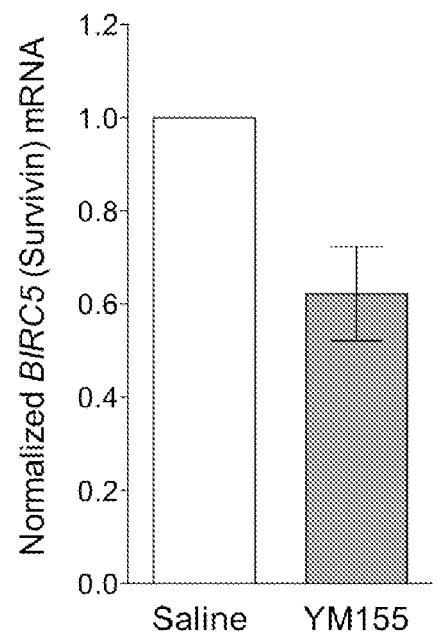
FIG. 12—Lower survivin levels in mice xenograft tumors treated with YM155. qRT-PCR for survivin from saline and YM155 (2 mg/kg) treated tumor tissues. Column represents mean and error bars represent standard deviation. Experiment was done in triplicate (Mean±SEM).

In contrast to bortezomib, YM155 (2 mg/kg, subcutaneous 5 times weekly (Nakahara et al., YM155, a novel small-molecule survivin suppressant, induces regression of established human hormone-refractory prostate tumor xenografts. *Cancer Res* 67, 8014 (Sep. 1, 2007); Nakahara et al., YM155, a novel survivin suppressant, enhances taxane-induced apoptosis and tumor regression in a human Calu 6 lung cancer xenograft model. *Anticancer Drugs* 22, 454 (June, 2011); Nakahara et al., Broad spectrum and potent antitumor activities of YM155, a novel small-molecule survivin suppressant, in a wide variety of human cancer cell lines and xenograft models. *Cancer Sci* 102, 614 (March, 2011)) markedly delayed MKL-1 xenograft growth and significantly prolonged survival compared to either saline or bortezomib (p value <0.0001, log-rank test, FIGS. 5B and 5C). FIG. 5B shows MKL-1 xenograft survival curves after drug treatment. Mice were subcutaneously injected with 20 million MKL-1 cells and assigned to three weeks drug treatment after tumors became palpable. No significant difference was found between saline and bortezomib treatment. Tumor progression was significantly delayed by YM155, with none of the YM155-treated mice dying during treatment (up to day 19) compared to 23 of 31 (74%) saline and 14 of 21 (67%) bortezomib-treated mice. Tumor progression recurred for all YM155-treated mice once treatment was stopped. Tumor progression recurred for all YM155-treated mice once treatment was stopped. FIG. 5C shows piecewise linear hierarchical Bayesian model for tumor volumes in treated mice (Zhao et al., Bayesian hierarchical changepoint methods in modeling the tumor growth profiles in xenograft experiments. *Clinical Cancer Research* 17, 1057 (Mar. 1, 2011)). Colored lines show estimated central population tumor volumes with shaded regions representing 95% credible intervals. Actual tumor volumes (grey lines) for each mouse are shown for comparison. YM155 treatment retards tumor growth compared to saline or bortezomib treatment. While 66.7-74.2% of bortezomib or saline-treated mice reached the euthanasia endpoint during the three-week treatment period, none of the YM155-treated mice reached this endpoint during treatment. Partial tumor regression occurred among some YM155-treated mice but all tumors resumed growth once YM155 was stopped, indicating that a single 3-week treatment course was insufficient for tumor eradication (FIG. 5B). For majority of the mice, MKL-1 tumor volumes were unchanged or showed delayed growth during YM155 treatment, suggesting this drug may be cytostatic rather than cytocidal for MKL-1 xenografts (FIG. 5C and FIG. 12). YM155 was well-tolerated and no adverse effects or acute toxicities were noted. In smaller cohorts of mice bearing MS-1 (MCV-positive) and UISO (MCV-negative) cell xenografts, final tumor volumes for YM155-treated mice were 43-55% (median) of saline-treated control mice at the end of the three week treatment period (FIG. 5D). FIG. 5D shows day of termination and tumor volumes for MS-1 and UISO xenograft mice used in the study.

Discussion

There is a common misperception that the human genome project failed to identify causes for human cancer or led to improved cancer treatments. We show here that discovery of a viral cause for most MCC in January 2008, which then led to description of the virus' oncogenes one year later, has been now used to rationally identify a survivin inhibitor that may have activity against this often intractable cancer. In contrast, our library screen of 1360 drugs, including the entire NCI Approved Oncology Drug Set II, confirms that MCC is very chemoresistant and identified only one other drug (bortezomib) that was highly active in vitro. Bortezomib, however was not active in vivo against MCC xenografts. DTS, a quantitative cDNA deep sequencing method, not only identified MCV as a new human polyomavirus but also helped to uncover cell signaling pathways perturbed by MCV oncogenes and have potential to be targets for MCV-positive MCC treatment.

Survivin, an inhibitor of apoptosis protein (IAP) family member, contributes to chemoresistance of melanoma and is overexpressed in many cancers including MCC. It is increased during non-neoplastic JC polyomavirus infection, and, through an E2F-regulated mechanism, by SV40 LT. Our MCV T antigen knockdown and expression experiments confirm survivin to be activated by MCV LT's sequestration of RB-family transcription repressors. Survivin has pleiotropic activities in both preventing apoptosis and activating cell cycle entry. Our findings are consistent with retinoblastoma protein or other pocket proteins repressing survivin expression in primary cells, which can be relieved when MCV LT is expressed. MCV LT did not further induce survivin in transformed cells in which retinoblastoma protein pathway signaling is already blocked by mutation, by E1A expression or other means. MCV induction of survivin may promote viral replication and survival by inhibiting innate immunity-induced cell death.

As seen herein, YM155 is highly cytotoxic in vitro to MCV-positive MCC cells, causing these cells to initiate a non-apoptotic programmed cell death routine (necroptosis). Loss of survivin is commonly linked to mitotic catastrophe in cancer cells; however, we did not find this to significantly contribute to MCC cell death. There was no distinct G1 or G2-M phase accumulation of cells during YM155 treatment and irreversible commitment to cell death occurs too quickly for most MCC cells to have an opportunity to transit the cell cycle. YM155 increases LC3-II, implicating autophagy in YM155-induced cell death. This is most likely a consequence rather than a cause for cell death but further studies are needed to establish this. Intriguingly, the cell death phenotype in MCC cells treated with YM155 is similar to that occurring when all T antigens are knocked down(27). Survivin inhibition alone may not be responsible for these effects since we were unable to rescue YM155 treated cells when survivin was expressed in a heterologous promoter and knock down of survivin alone in MCV-positive MCC causes apoptosis rather than necroptosis.

There are several important caveats to our current study. While YM155 was highly active in vitro, it was only cytostatic—not cytotoxic—in most mouse xenografts. Once YM155 treatment was stopped, tumors re-emerged in all of the treated mice. Either prolonged YM155 treatment or combined use with other drugs (e.g., bortezomib, topoisomerase inhibitors) may more effectively control MCC. YM155 was relatively nontoxic in our study, making it more suitable for prolonged or combined therapy. Practical limitations prevented us from extensively measuring YM155 activity on a variety of MCC cell line xenografts and we cannot exclude the possibility of resistance among other MCC. But it is encouraging that YM155 reduced tumor masses in two additional MCC xenografts, including one from a MCV-negative tumor. Finally, MCV sT (also expressed in MCC cells) increases cap-dependent protein translation, and could contribute to YM155 resistance.

DTS is a useful method to discover or exclude viruses being present in human cancers. In this study, we show that DTS is also useful in measuring cellular gene expression by demonstrating that BIRC5 transcription is activated in MCV-positive MCC. If carefully performed and rigorously analyzed, DTS data yields useful information even when no cancer viruses are discovered. Prior to discovery of MCV, few clues were available about the molecular causes for MCC. Now that MCV has been shown to be central to most MCC, rational targeting of cellular pathways perturbed by MCV may lead to discovery of additional treatments that may be more effective and less toxic than current therapies.

Example 2

To follow up on the results obtained in Experiment 1, other MCC polyomavirus (+) cell lines were utilized as xenografts in vivo to test the ability of YM155 to prolong survival.

Materials

Clinical-grade bortezomib (Velcade) was purchased from the University of Pittsburgh Cancer Institute Pharmacy and YM155 was purchased from Active Biochemicals Ltd. (Hong Kong, China). Compounds were dissolved in sterile 0.9% saline solution for administration to animals.

Animals

Six-week-old female triple immune-deficient NSG (Nod-SCID gamma) mice (Jackson Laboratory) were maintained in a specific pathogen-free environment.

Xenograft Drug Treatments

Cells of Merkel cell polyomavirus (+) carcinoma cell lines MKL-1, MS-1, WaGa, and MKL-2 were checked for viability >90% by trypan blue staining, resuspended in PBS ($2\times10^7$ cells in 100 µl) and inoculated subcutaneously into the right flank of mice. Once tumors were palpable (2-4 weeks after injection) (FIG. 13), mice were assigned sequentially into the following groups: For animals receiving MKL-1 cells, saline (n=43), 1 mg/kg bortezomib for three weeks (n=21), 2 mg/kg YM155 for 3 weeks (n=34), 2 mg/kg of continuous YM155 (n=20), and 4 mg/kg of continuous YM155 (n=20); For animals receiving MS-1 cells, saline (n=14), 2 mg/kg of continuous YM155 (n=10), and 4 mg/kg continuous YM155 (n=10); For animals receiving WaGa cells, saline (n=10) and 4 mg/kg continuous YM155 (n=11); and For animals receiving MKL-2 cells, saline (n=10) and 4 mg/kg continuous YM155 (n=10).

Bortezomib treatment was delivered subcutaneously twice weekly at 1 mg/kg per mouse. To avoid previously observed side effects, mice were given hydrogel (ClearH$_2$O) and kept at 30° C. (using a heating blanket to heat up half of the cage) during bortezomib treatment. YM-155 was given intraperitoneally on five consecutive days, followed by a two-day treatment free interval. For YM155 this treatment continued for three weeks or until mice were euthanized. Mice were euthanized upon showing a tumor having a diameter of 20 mm, or upon a showing of significant distress (>20% weight loss or when they became moribund). Caliper measurements of the longest perpendicular tumor diameters were performed every other day and tumor volumes were calculated using the formula: (width)$^2$×(length/2). Survival was defined as time from the first day of treatment until death/sacrifice.

Results

Figure 13:
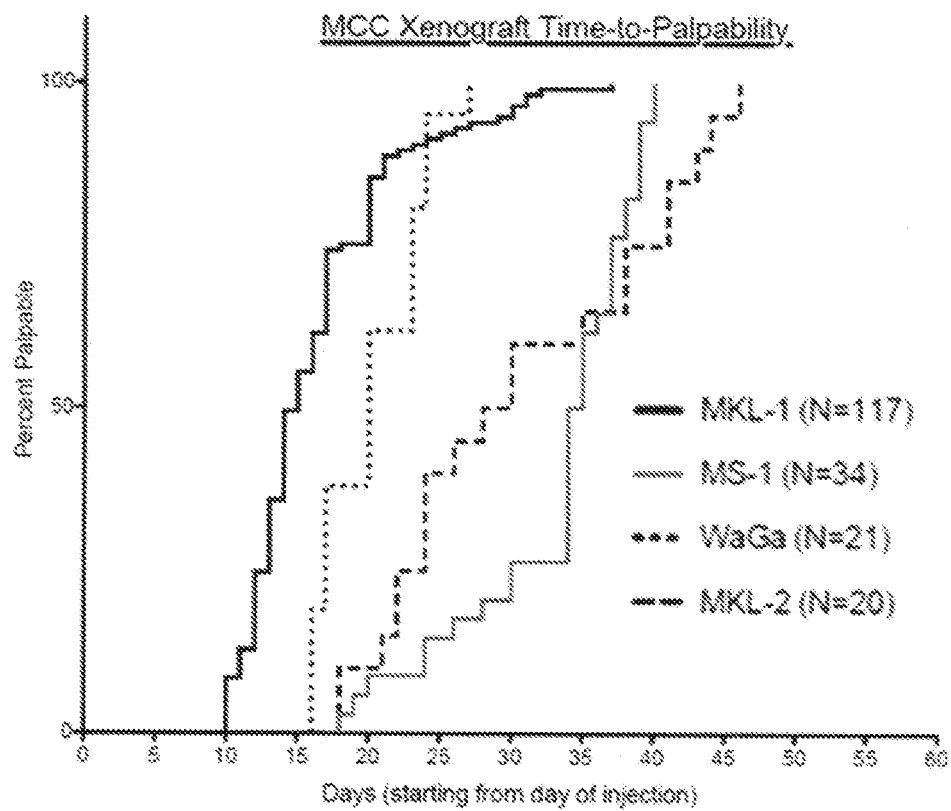
FIG. 13—Graph showing time from injection of MKL-1, MS-1, WaGa, or MKL-2 cells into a mouse to detection of a palpable tumor.
Figure 14:
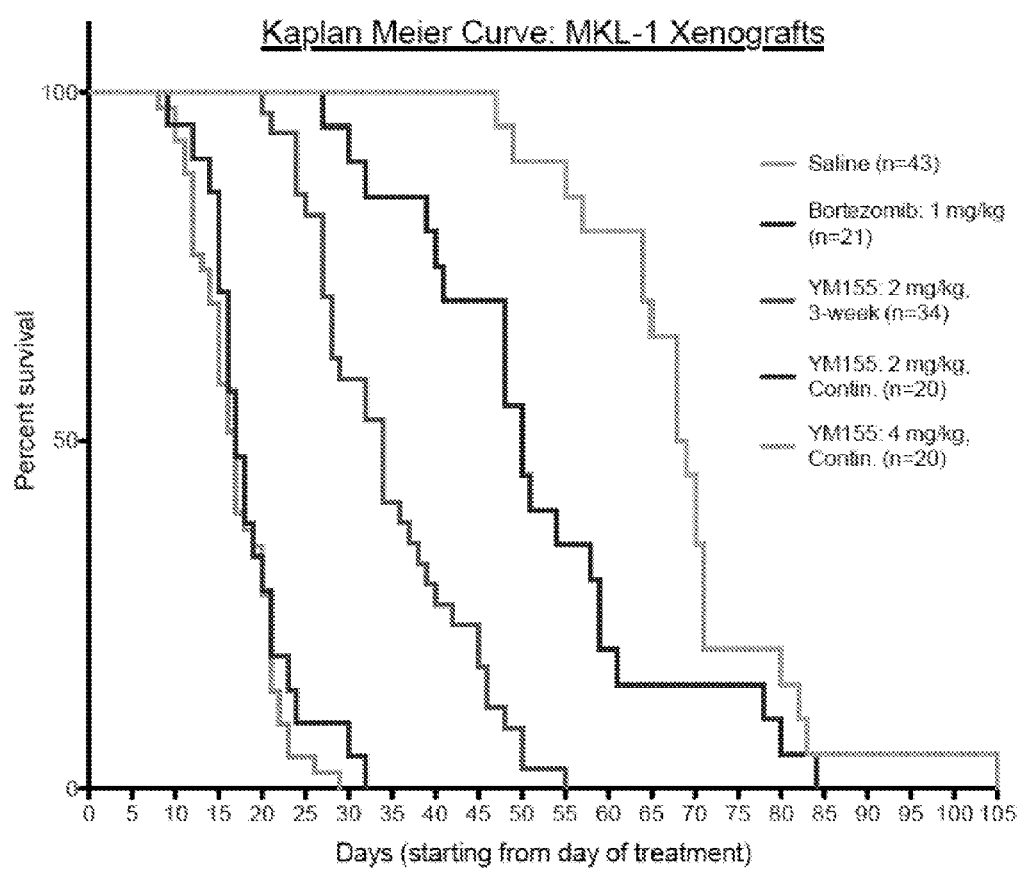
FIG. 14—Kaplan Meier Curve showing percent survival of animals with MKL-1 xenografts treated with saline, bortezomib, or YM155 at 2 mg/kg or 4 mg/kg for 3 weeks or continuously.
Figure 15:
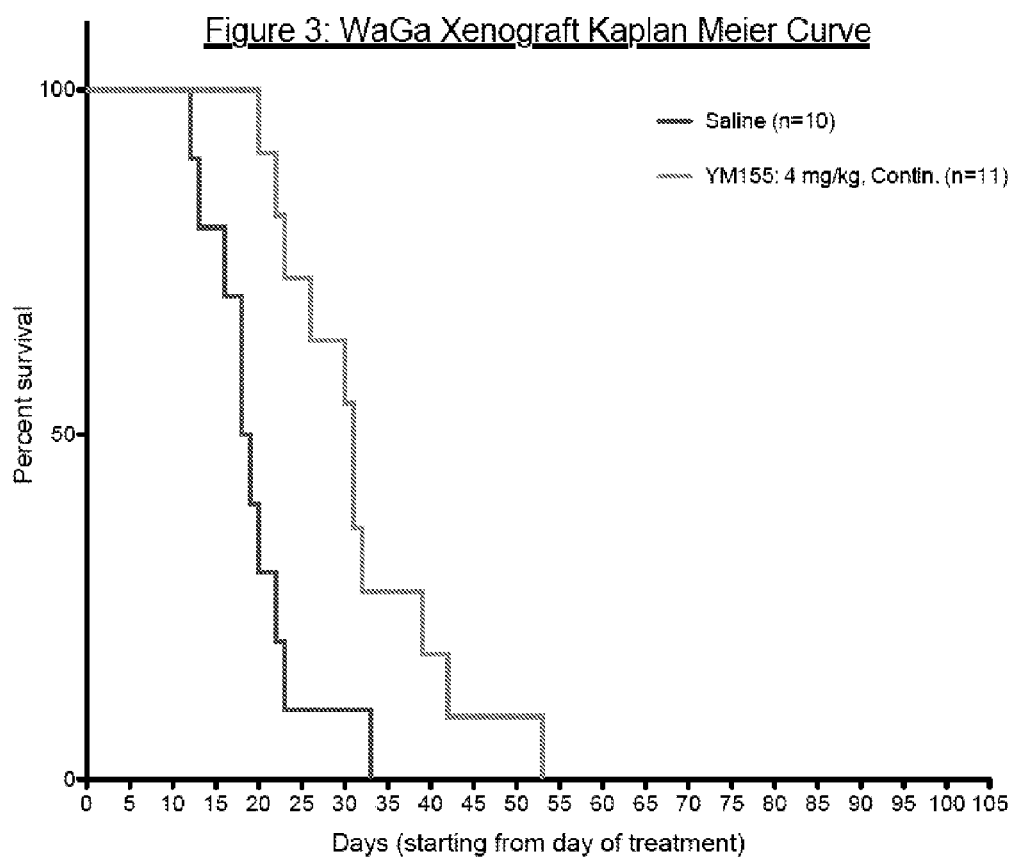
FIG. 15—Kaplan Meier Curve showing percent survival of animals with WaGa xenografts treated with saline or YM155 continuously at 4 mg/kg.
Figure 16:
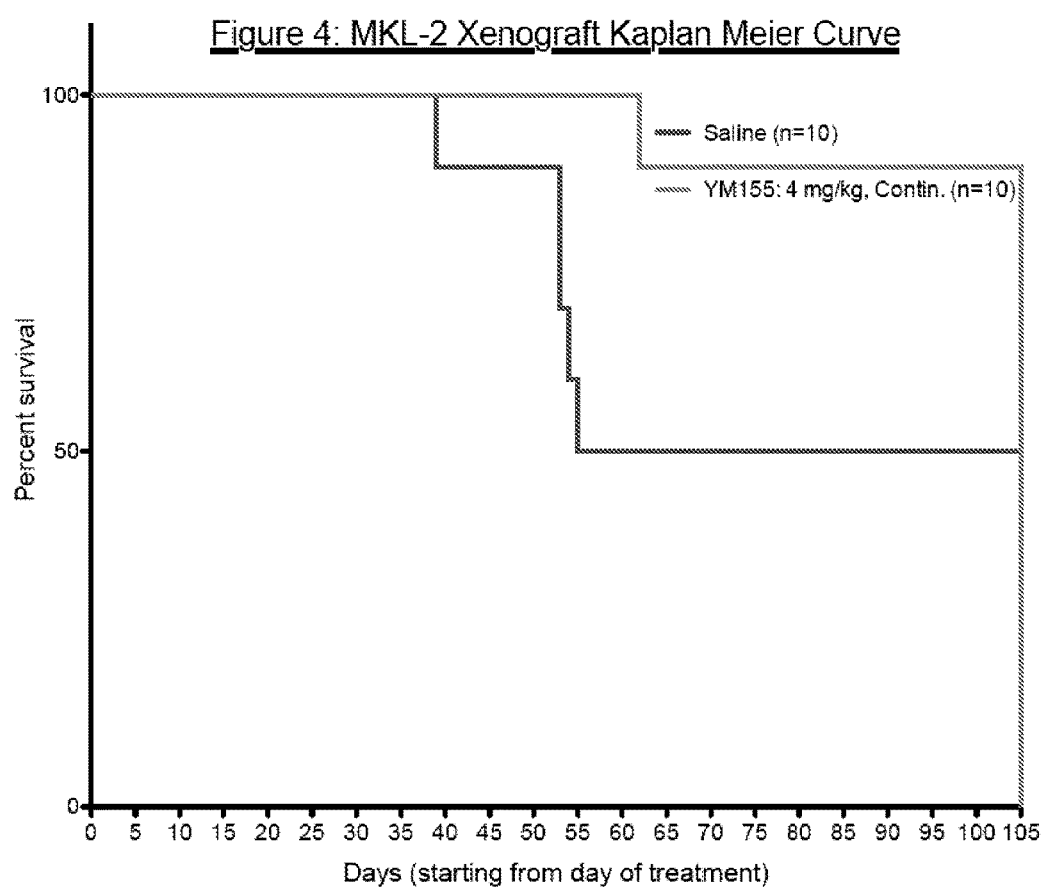
FIG. 16—Kaplan Meier Curve showing percent survival of animals with MKL-2 xenografts treated with saline or YM155 continuously at 4 mg/kg.

FIG. 13 shows the time course from injection of the identified cell lines (MKL-1, MS-1, WaGa, MKL-2) to the time that the tumor was palpable. Treatment with saline, bortezomib, or YM155 began at the time that the tumors were palpable. FIG. 14 shows that animals with MKL-1 xenografts treated with bortezomib survived as long as those receiving saline. The last animal to receive bortezomib died approximately one month after treatment began. In contrast, animals receiving YM155 survived for significantly longer, from almost two months after initiation of treatment (YM155 at 2 mg/kg for three weeks) to more than three months after treatment began (YM155 continuously at 4 mg/kg). Similar results were seen in WaGa cell-inoculated animals (FIG. 15). In mice with MKL-2 xenografts, of the 10 animals that received YM155 continuously at 4 mg/kg, three survived more than four months, and at present have not succumbed to the tumor (FIG. 16).

Discussion

The results of the experiments in mice with xenografts are notable for a number of reasons. First, the results show that YM155, which causes downregulation of survivin, possibly through interaction with the ILF3/p54$^{nrb}$ complex, significantly increases survival of mice with xenografts from different MCC cell lines. Second, the results are notable because the mice did not have the tumor resected or debulked at any time prior to or following initation of YM155 treatment. Accordingly, YM155 was able to prolong lifespan in animals in which the xenograft continued to grow. Third, xenografts in a mouse model are widely acknowledged as difficult to cure, and the prolonging of life in this model is an exceptional result. Fourth, the dosage administered to the mice was fairly small (2 or 4 mg/kg, once a day for three weeks or until death). Humans are likely to be able to tolerate much higher doses, as seen in descriptions of phase I studies and phase II trials of YM155 for treatment of late-stage melanoma. Lastly, the dosing regimen in humans can be continuous, for example through provision of a catheter and a programmable pump, or otherwise optimized while administration to the mice in these experiments was administered as a single intraperitoneal bolus.

We claim:

1. A method of treating a polyomavirus (+) cancer in which survivin is upregulated in a patient, comprising administering to the patient a therapeutically effective amount of a composition comprising a compound having the structure:

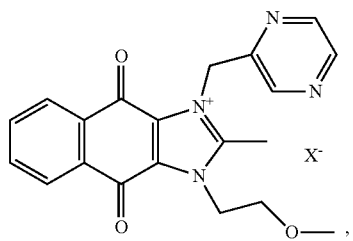

wherein X is a pharmaceutically acceptable counterion.

2. The method of claim 1, in which the polyomavirus (+) cancer is a Merkel cell polyomavirus (+) Merkel cell carcinoma and the composition comprises YM155.

3. The method of claim 1, wherein the polyomavirus (+) cancer is a polyomavirus (+) Merkel cell carcinoma.

4. The method of claim 1, wherein the polyomavirus (+) cancer is caused by JC virus, BK virus, Karolinska institute virus, or Washington University virus.

5. The method of claim 1, wherein the compound is YM155.

6. The method of claim 1, wherein the composition comprises one or more additional active agents.

7. The method of claim 6, in which the one or more additional active agent is one or more of an anticancer chemotherapeutic agent, an antibiotic, a protein-based therapeutic, an antibody or fragment thereof, an antiemetic, a cell-based therapeutic, a cell-based immunotherapeutic, or a vector comprising a gene for producing a therapeutic or immunotherapeutic composition.

8. The method of claim 1, in which the composition comprises an interfering nucleic acid.

9. The method of claim 8, in which the interfering nucleic acid targets one of survivin, ILF3, p54nrb or polyomavirus T antigen.

10. The method of claim 1, comprising administering the composition to the patient in an amount of from about 2 mg/kg per day to about 10 mg/kg per day.

11. The method of claim 10, wherein the composition is administered on from one to seven days weekly.

12. The method of claim 10, comprising administering YM155 to the patient in an amount of about 2 mg/kg about five times weekly to the patient.

13. A method of reducing growth of polyomavirus (+) cancer cells in which survivin is up-regulated, comprising contacting the cells with a composition comprising a compound having the structure:

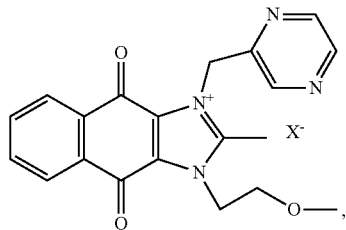

wherein X is a pharmaceutically acceptable counterion, in an amount effective to reduce growth of the cells.

14. The method of claim 13, in which the composition is YM155.

15. The method of claim 14, in which the cells are in vitro.

* * * * *

UNITED STATES PATENT AND TRADEMARK OFFICE
CERTIFICATE OF CORRECTION

| | | |
|---|---|---|
| PATENT NO. | : 9,662,329 B2 | Page 1 of 1 |
| APPLICATION NO. | : 14/388418 | |
| DATED | : May 30, 2017 | |
| INVENTOR(S) | : Yuan Chang et al. | |

It is certified that error appears in the above-identified patent and that said Letters Patent is hereby corrected as shown below:

In the Specification

Column 1, Lines 17 through 19, delete "This work was supported by National Institutes of Health Grant CA120726 and CA136363. The United States government has certain rights in the invention." and insert -- This invention was made with government support under grant numbers CA120726 and CA136363 awarded by the National Institutes of Health. The government has certain rights in the invention. --

Signed and Sealed this
Twenty-third Day of April, 2019

Andrei Iancu
*Director of the United States Patent and Trademark Office*